United States Patent
Upton

(10) Patent No.: US 9,562,086 B2
(45) Date of Patent: Feb. 7, 2017

(54) VITRONECTIN:KERATINOCYTE GROWTH FACTOR CHIMERAS

(75) Inventor: Zee Upton, Indooropilly (AU)

(73) Assignee: QUEENSLAND UNIVERSITY OF TECHNOLOGY, Brisbane (AU)

( * ) Notice: Subject to any disclaimer, the term of this patent is extended or adjusted under 35 U.S.C. 154(b) by 0 days.

(21) Appl. No.: 13/701,472

(22) PCT Filed: Jun. 3, 2011

(86) PCT No.: PCT/AU2011/000700
§ 371 (c)(1),
(2), (4) Date: May 3, 2013

(87) PCT Pub. No.: WO2011/150470
PCT Pub. Date: Dec. 8, 2011

(65) Prior Publication Data
US 2013/0243843 A1 Sep. 19, 2013

Related U.S. Application Data

(63) Continuation of application No. 12/793,386, filed on Jun. 3, 2010.

(51) Int. Cl.
| | |
|---|---|
| *C07K 14/50* | (2006.01) |
| *C07K 14/475* | (2006.01) |
| *C07K 14/435* | (2006.01) |
| *C07K 16/28* | (2006.01) |
| *A61K 38/00* | (2006.01) |

(52) U.S. Cl.
CPC .............. *C07K 14/50* (2013.01); *C07K 14/435* (2013.01); *C07K 14/475* (2013.01); *C07K 16/2839* (2013.01); *A61K 38/00* (2013.01); *C07K 2317/76* (2013.01); *C07K 2319/00* (2013.01); *C07K 2319/50* (2013.01)

(58) Field of Classification Search
None
See application file for complete search history.

(56) References Cited

U.S. PATENT DOCUMENTS

| | | | |
|---|---|---|---|
| 8,871,709 B2 | 10/2014 | Upton et al. | |
| 2006/0194292 A1* | 8/2006 | Upton | C07K 14/65 435/69.7 |

FOREIGN PATENT DOCUMENTS

| | | | | |
|---|---|---|---|---|
| AU | WO 02/24219 | * | 3/2002 | ............ A61K 38/39 |
| AU | WO2004/069871 | * | 8/2004 | ............ C07K 14/61 |
| WO | WO2004/023973 | * | 3/2004 | |
| WO | 2008157483 A2 | | 12/2008 | |
| WO | 2011063477 A1 | | 6/2011 | |

OTHER PUBLICATIONS

Phillips, A., J Pharm Pharmacology, 2001; 53: 1169-1174.*
Staiano-Coico et al., J Exp Med, 1993; 178: 865-78.*
Schoppet et al., Lab Invest. 2002; 82: 37-46.*
Liu et al., Invest Opthalmol Vis Sci, 1998; 39: 2584-2593.*
Ainscough S L et al: "Vitronectin supports migratory responses of corneal epithelial cells to substrate bound IGF-1 3nd HGF, and facilitates serum-free cultivation",EXPEW1ENTAL Eye Research, Academic Press Eye Research, L to, London, vol. 83, No. 6, Dec. 1, 2006 (Dec. 1, 2006), pp. 1505-1514, XP024945625, ISSN: 0014-4835, DOI: 10.1016/J.EXER.2006.08.012 [retrieved on Dec. 1, 2006).
Guo et al. Keratinocyte Growth Factor is Required for Hair Development but not for Wound Healing. Genes Dev., vol. 10, No. 2 (Jan. 15, 1996), pp. 165-175.
Hyde, C. et al., 'Insulin-like growth factors (IGF) and IGF-binding proteins bound to vitronectin enhance keratinocyte protein synthesis and migration', Journal of Investigative Dermatology, 2004, vol. 122, pp. 1198-1206.

* cited by examiner

*Primary Examiner* — Christina Borgeest
(74) *Attorney, Agent, or Firm* — Faegre Baker Daniels LLP

(57) ABSTRACT

Isolated protein complexes are provided comprising keratinocyte growth factor and vitronectin, or at least domains thereof that enable binding to and activation of both a keratinocyte growth factor receptor and an integrin receptor for vitronectin. These protein complexes include synthetic proteins where the keratinocyte growth factor and vitronectin sequences are joined by a linker sequence. In particular forms, vitronectin sequences do not include a C-terminal heparin binding domain. Also provided are uses of these protein complexes for stimulating or inducing cell migration and/or proliferation in wound healing, tissue engineering, cosmetic and therapeutic treatments such as skin replacement, skin replenishment and treatment of burns where epithelial cell migration is required. In other embodiments, the invention provides inhibition of cancer cell metastasis, particularly in relation to breast cancer.

18 Claims, 6 Drawing Sheets

| Amino acid sequence of full length vitronectin (including signal peptide) |
|---|
| 1 maplrpllil allawvalad qesckgrcte gfnvdkkcqc delcsyyqsc ctdytaeckp
61 qvtrgdvftm pedeytvydd qeeknnatvh eqvggpslts dlqaqskgnp eqtpvlkpee
121 eapapevgas kpegidsrpe tlhpgrpqpp aeeelcsgkp fdaftdlkng slfafrgqyc
181 yeldekavrp gypklirdvw giegpidaaf trincqgkty lfkgsqywrf edgvldpdyp
241 rnisdgfdgi pdnvdaalal pahsysgrer vyffkgkqyw eyqfqhqpsq eecegsslsa
301 vfehfammqr dswedifell fwgrtsagtr qpqfisrdwh gvpgqvdaam agriyisgma
361 prpslakkqr frhrnrkgyr sqrghsrgrn qnsrrpsram wlslfssees nigannyddy
421 rmdwlvpatc epiqsvfffs gdkyyrvnlr trrvdtvdpp yprsiaqywl gcpapghl
(SEQ ID NO:1) |

| Domain Structure | Residues† | Residues‡ |
|---|---|---|
| Signal Peptide | | 1-19 |
| Somatomedin B domain | 1-44 | 20-63 |
| RGD Motif | 45-47 | 64-66 |
| Polyanionic (acidic) region | 53-64 | 72-83 |
| Hemopexin-like repeats (x2) | 131-459 | 150-478 |
| - Central 4-bladed propeller domain | 131-342 | 150-361 |
| - C-terminal heparin binding domain | 347-459 | 366-478 |
| Polycationic (basic) region | 348-379 | 367-398 |

| Residue Modification Sites | Residues† | Residues‡ |
|---|---|---|
| cAMP-dependant PK phosphorylation site | 378 | 397 |
| Sulphated tyrosine residues (x2) | 56, 59 | 75, 78 |
| PKC phosphorylation site | 362 | 381 |
| Casein kinase phosphorylation site (x2) | 50, 57 | 69, 76 |

| Protease Recognition Sites | Residues† | Residues‡ |
|---|---|---|
| Endogenous cleavage site(unidentified protease) | 379-380 | 398-399 |
| Thrombin cleavage site | 305-306 | 324-325 |
| Thrombin cleavage site | 370-371 | 389-390 |
| Elastase cleavage site | 330-331 | 349-350 |
| Elastase cleavage site | 383-384 | 402-403 |
| Plasmin cleavage site | 361-362 | 380-381 |

| Substrate Binding Sites | Residues† | Residues‡ |
|---|---|---|
| PAI-1 | 12-30 | |
| PAI-1 | 348-370 | |
| uPAR | SomB region | |
| Integrin | 45-47 | |
| Collagen | Polycationic region | |
| Collagen | Polyanionic region | |
| Thrombin antithrombin III complex | Polycationic region | |
| Plasminogen | 332-348 | |
| Glycosaminoglycan | 348-361 | |

† Residues numbered according to their position on the mature protein
‡ Residues numbered according to their position on the pro-protein (with signal peptide)

Figure 1

A) VN AA sequence

```
dqesckgrct egfnvdkkcq cdelcsyyqs cctdytaeck pqvtrgdvft mpedeytvyd
dgeeknnatv heqvggpslt sdlqaqskgn peqtpvlkpe eeapapevga skpegidsrp
etlhpgrpqp paeeelcsgk pfdaftdlkn gslfafrgqy cyeldekavr pgypklirdv
wgiegpidaa ftrincqgkt ylfkgsqywr fedgvldpdy prnisdgfdg ipdnvdaala
lpahsysgre rvyffkgkqy weyqfqhqps qeecegssls avfehfammq rdswedifel
lfwgrtsagt rqpqfisrdw hgvpgqvdaa magriyisgm aprpslakkq rfrhrnrkgy
rsqrghsrgr nqnsrrpsra twlslfssee snlgannydd yrmdwlvpat cepiqsvfff
sgdkyyrvnl rtrrvdtvdp pyprsiaqyw lgcpapghl (SEQ ID NO:2)
```

B) KGF AA sequence

```
CNDMTPEQMA TNVNCSSPER HTRSYDYMEG GDIRVRRLFC RTQWYLRIDK RGKVKGTQEM
KNNYNIMEIR TVAVGIVAIK GVESEFYLAM NKEGKLYAKK ECNEDCNFKE LILENHYNTY
ASAKWTHNGG EMFVALNQKG IPVRGKKTKK EQKTAHFLPM AIT (SEQ ID NO:3)
```

C) Linker Sequences

1)  Gly$_4$ Ser (SEQ ID NO:4)

2)  Gly$_4$ Ser$_3$ (SEQ ID NO:5)

3)  (Gly$_4$ Ser)$_3$ (SEQ ID NO:6)

4)  (Gly$_4$ Ser)$_4$ (SEQ ID NO:7)

5)  Leu Ile Lys Met Lys Pro (SEQ ID NO:8)

6)  Gln Pro Gln Gly Leu Ala Lys (SEQ ID NO:9)

D) 1-459VN:(G$_4$S)$_4$:1-163KGF:G$_4$SG$_4$:6H

```
DQESCKGRCTEGFNVDKKCQCDELCSYYQSCCTDYTAECKPQVTRGDVFTMPEDEYTVYDDGEEKNNATVH
EQVGGPSLTSDLQAQSKGNPEQTPVLKPEEEAPAPEVGASKPEGIDSRPETLHPGRPQPPAEEELCSGKPF
DAFTDLKNGSLFAFRGQYCYELDEKAVRPGYPKLIRDVWGIEGPIDAAFTRINCQGKTYLFKGSQYWRFED
GVLDPDYPRNISDGFDGIPDNVDAALALPAHSYSGRERVYFFKGKQYWEYQFQHQPSQEECEGSSLSAVFE
HFAMMQRDSWEDIFELLFWGRTSAGTRQPQFISRDWHGVPGQVDAAMAGRIYISGMAPRPSLAKKQRFRHR
NRKGYRSQRGHSRGRNQNSRRPSRAMWLSLFSSEESNLGANNYDDYRMDWLVPATCEPIQSVFFFSGDKYY
RVNLRTRRVDTVDPPYPRSIAQYWLGCPAPGHLGGGGSGGGGSGGGGSGGGGSCNDMTPEQMATNVNCSSP
ERHTRSYDYMEGGDIRVRRLFCRTQWYLRIDKRGKVKGTQEMKNNYNIMEIRTVAVGIVAIKGVESEFYLA
MNKEGKLYAKKECNEDCNFKELILENHYNTYASAKWTHNGGEMFVALNQKGIPVRGKKTKKEQKTAHFLPM
AITGGGGSGGGGHHHHHH (SEQ ID NO:10)
```

Figure 3

E) 1-311VN:(G₄S)₄:1-163KGF:G₄SG₄:6H

DQESCKGRCTEGFNVDKKCQCDELCSYYQSCCTDYTAECKPQVTRGDVFTMPEDEYTVYDDGEEKNNATVH
EQVGGPSLTSDLQAQSKGNPEQTPVLKPEEEAPAPEVGASKPEGIDSRPETLHPGRPQPPAEEELCSGKPF
DAFTDLKNGSLFAFRGQYCYELDEKAVRPGYPKLIRDVWGIEGPIDAAFTRINCQGKTYLFKGSQYWRFED
GVLDPDYPRNISDGFDGIPDNVDAALALPAHSYSGRERVYFFKGKQYWEYQFQHQPSQEECEGSSLSAVFE
HFAMMQRDSWEDIFELLFWGRTSAGTRGGGGSGGGGSGGGGSGGGGSCNDMTPEQMATNVNCSSPERHTRS
YDYMEGGDIRVRRLFCRTQWYLRIDKRGKVKGTQEMKNNYNIMEIRTVAVGIVAIKGVESEFYLAMNKEGK
LYAKKECNEDCNFKELILENHYNTYASAKWTHNGGEMFVALNQKGIPVRGKKTKKEQKTAHFLPMAITGGG
GSGGGGHHHHHH (SEQ ID NO:11)

F) 1-125VN:(G₄S)₄:1-163KGF:G₄SG₄:6H

DQESCKGRCTEGFNVDKKCQCDELCSYYQSCCTDYTAECKPQVTRGDVFTMPEDEYTVYDDGEEKNNATVH
EQVGGPSLTSDLQAQSKGNPEQTPVLKPEEEAPAPEVGASKPEGIDSRPETLHPGGGGSGGGGSGGGGSG
GGGSCNDMTPEQMATNVNCSSPERHTRSYDYMEGGDIRVRRLFCRTQWYLRIDKRGKVKGTQEMKNNYNIM
EIRTVAVGIVAIKGVESEFYLAMNKEGKLYAKKECNEDCNFKELILENHYNTYASAKWTHNGGEMFVALNQ
KGIPVRGKKTKKEQKTAHFLPMAITGGGSGGGGHHHHHH (SEQ ID NO:12)

G) 1-64VN:(G₄S)₄:1-163KGF:G₄SG₄:6H

DQESCKGRCTEGFNVDKKCQCDELCSYYQSCCTDYTAECKPQVTRGDVFTMPEDEYTVYDDGEEGGGGSGG
GGSGGGGSGGGGSCNDMTPEQMATNVNCSSPERHTRSYDYMEGGDIRVRRLFCRTQWYLRIDKRGKVKGTQ
EMKNNYNIMEIRTVAVGIVAIKGVESEFYLAMNKEGKLYAKKECNEDCNFKELILENHYNTYASAKWTHNG
GEMFVALNQKGIPVRGKKTKKEQKTAHFLPMAITGGGSGGGGHHHHHH (SEQ ID NO:13)

H) 1-64VN:(G₄S)₄: 343-376VN:(G₄S)₄:1-163KGF:G₄SG₄:6H

DQESCKGRCTEGFNVDKKCQCDELCSYYQSCCTDYTAECKPQVTRGDVFTMPEDEYTVYDDGEEGGGGSGG
GGSGGGGSGGGGSRPSLAKKQRFRHRNRKGYRSQRGHSRGRNQNSRRGGGGSGGGGSGGGGSGGGGSCNDM
TPEQMATNVNCSSPERHTRSYDYMEGGDIRVRRLFCRTQWYLRIDKRGKVKGTQEMKNNYNIMEIRTVAVG
IVAIKGVESEFYLAMNKEGKLYAKKECNEDCNFKELILENHYNTYASAKWTHNGGEMFVALNQKGIPVRGK
KTKKEQKTAHFLPMAITGGGSGGGGHHHHHH (SEQ ID NO:14)

VITRONECTIN:KERATINOCYTE GROWTH FACTOR CHIMERAS

CROSS-REFERENCE TO RELATED APPLICATIONS

This is a national phase filing, pursuant to 35 U.S.C. §371, of PCT application No. PCT/AU2011/000700, filed on Jun. 3, 2011, which claims the benefit of U.S. application Ser. No. 12/793,386, filed on Jun. 3, 2010. The prior applications are incorporated herein by reference in their entirety.

FIELD OF THE INVENTION

THIS INVENTION relates to protein complexes having respective domains that enable binding to and activation of both a keratinocyte growth factor (KGF) receptor and an integrin receptor for vitronectin (VN). In particular embodiments, this invention relates to chimeric proteins comprising keratinocyte growth factor receptor-binding domains and an integrin receptor-binding domain of vitronectin. More particularly, this invention relates to protein complexes and chimeric proteins that stimulate cell migration and to compositions and methods that promote or induce cell migration and/or proliferation. These compositions and methods have use in wound healing, tissue engineering, cosmetic and therapeutic treatments such as skin replacement, and skin replenishment and treatment of burns where epithelial cell migration and/or proliferation is required. In other embodiments, the invention provides treatment provided by the present invention related to prevention or inhibition of cancer cell metastasis, particularly in relation to breast cancer.

BACKGROUND OF THE INVENTION

Keratinocyte growth factor is a mitogenic peptide growth factor involved in a broad range of cellular processes including hyperplasia, DNA synthesis, differentiation, cell cycle progression, and inhibition of apoptosis (Marchese et al., 1990, J. Cell Physiol. 144:326-32). These effects are mediated through binding to its tyrosine-kinase linked cell surface receptor, the KGF receptor.

Vitronectin is a glycoprotein that is highly abundant in the blood and in the extra cellular matrix (ECM). Primarily synthesized in the liver, but expressed by many other cell types, VN circulates in the blood in a closed conformation and is deposited in the ECM in an open, or extended, conformation (Schvartz et al., 1999, Int. J. Biochem. Cell Biol. 31:531-44). Both conformations are believed to bind IGF-II (Upton et al., 1999, Endocrinology 140:2928-31; International Publication WO 02/24219; McMurty et al., 1996, Endocrinology 150:149-60) and also bind multiple other ligands including collagen (Morris et al., 1994, J. Bio. Chem. 269:23845-52), glycosaminoglycans (Francois et al., 1999, J. Bio. Chem. 274:37611-19), many other ECM proteins, and a wide variety of integrins, particularly the $\alpha_v$ integrins. Indeed, the primary role of vitronectin is as an ECM organization molecule that provides adhesive links to these cell surface integrin receptors via an RGD binding motif. The VN receptors ($\alpha_v$ integrins) have been shown to regulate the actin cytoskeleton rearrangement required for growth and invasion, hence, VN binding coordinates cell adhesion and movement (DePasquale, 1998, Histochemistry and Cell Biology 110:485-94; Huang, 2000, Oncogene 19:1915-23).

However, the relative contributions of KGF and VN, and their respective domains, present in protein complexes, in terms of stimulating biological responses such as cell migration and/or proliferation, have remained elusive.

SUMMARY OF THE INVENTION

The present inventors have discovered that protein complexes comprising KGF and VN stimulate cell migration and/or proliferation by binding and synergistically co-activating keratinocyte growth factor receptors and VN-binding integrin receptors.

Therefore, the invention is broadly directed to isolated protein complexes that comprise a receptor-binding domain of keratinocyte growth factor and a domain of vitronectin that is capable of binding an integrin receptor, wherein the isolated protein complex can co-activate the keratinocyte growth factor receptor and integrin receptor to thereby elicit a biological response.

In a first aspect, the invention provides an isolated protein complex in the form of a synthetic chimeric protein comprising an amino acid sequence of:

(i) keratinocyte growth factor, or at least a domain of keratinocyte growth factor which is capable of binding a keratinocyte growth factor receptor; and (ii) one, or more domains of vitronectin (VN) including at least an integrin-binding domain of VN.

Preferably, the integrin receptor is an $\alpha_v$ integrin.

More preferably, the integrin receptor is an $\alpha_v\beta_3$ integrin or an $\alpha_v\beta_5$ integrin.

This aspect of the invention also includes within its scope amino acid deletions, additions, substitutions and/or mutations of amino acid sequences corresponding to (i) and (ii) above.

In a second aspect, the invention provides an isolated nucleic acid encoding the isolated protein complex of the first aspect.

In a third aspect, the invention provides a genetic construct comprising the isolated nucleic acid of the second aspect operably linked to one or more regulatory sequences in an expression vector.

Preferably, the genetic construct is an expression construct.

In a fourth aspect, the invention provides a host cell comprising the genetic construct of the third aspect.

In a fifth aspect, the invention provides a pharmaceutical composition comprising the isolated protein complex of the first aspect and a pharmaceutically-acceptable carrier, diluent or excipient.

This aspect of the invention also contemplates a pharmaceutical composition comprising the host cell of the fourth aspect, which cell expresses said synthetic protein(s).

In a sixth aspect, the invention provides an antibody specific for the synthetic protein of the first aspect.

In a seventh aspect, the invention provides a method of promoting cell migration including the step of using a synthetic protein to bind both a keratinocyte growth factor receptor and an integrin receptor.

Preferably, the integrin receptor is an cc, integrin.

More preferably, the integrin receptor is an $\alpha_v\beta_3$ integrin or an $\alpha_v\beta_5$ integrin.

In a preferred embodiment, this aspect of the invention relates to promotion or induction of epithelial/keratinocyte/fibroblast cell migration and/or proliferation to facilitate wound healing in mammals, preferably humans.

Preferably, said synthetic protein is as according to the first aspect of the invention.

In an eighth aspect, the invention provides a method of preventing cell migration and/or proliferation, including the step of preventing, inhibiting or otherwise reducing binding of both a keratinocyte growth factor receptor and an integrin receptor by a complex comprising keratinocyte growth factor and vitronectin.

Preferably, the integrin receptor is an $\alpha_v$ integrin.

More preferably, the integrin receptor is an $\alpha_v\beta_3$ integrin or an $\alpha_v\beta_5$ integrin.

In a preferred embodiment, this aspect of the invention relates to prevention or inhibition of metastatic cancer cell migration and/or proliferation in mammals, preferably humans.

A particular example contemplated by this aspect of the invention is prevention or inhibition of breast cancer metastasis.

It will also be appreciated that the methods of the seventh and eighth aspects may encompass prophylactic and therapeutic methods of treatment.

In a ninth aspect, the invention provides use of the isolated protein complex of the first aspect to produce a molecule that:

(i) is an agonist of protein complexes comprising keratinocyte growth factor and vitronectin; or (ii) is an antagonist of protein complexes comprising keratinocyte growth factor and vitronectin.

In one embodiment, the invention provides use of the synthetic protein of the first aspect to produce a molecule that:

(i) is an agonist of KGF:VN protein complexes; or (ii) is an antagonist of KGF:VN protein complexes.

Agonists and/or antagonists produced according to this aspect of the invention may have particular efficacy in promoting wound healing, tissue engineering, skin regeneration and/or prevention of cancer cell metastasis or hyperproliferative disorders of the skin, such as scarring and psoriasis.

In a tenth aspect, the invention provides a biomaterial that comprises the isolated protein complex of the first aspect.

In particular embodiments the biomaterial may be a surgical implant, prosthesis, scaffold, wound or burn dressing, or the like suitably impregnated, coated or otherwise comprising an isolated protein complex of the invention.

BRIEF DESCRIPTION OF THE FIGURES

FIG. 1. The amino acid sequence of vitronectin (SEQ ID NO:1), including residue references for the various domains within vitronectin, as well as residue modification sites, ligand binding sites and protease recognition sites.

FIG. 3. Amino acid sequence of (A) mature vitronectin protein (SEQ ID NO:2), (B) mature KGF (SEQ ID NO:3), (C) preferred linker sequences (SEQ ID NOs:4-9), and (D) to (H) embodiments of KGF and VN-containing chimeric proteins (SEQ ID NOs:10-14).

DETAILED DESCRIPTION OF THE INVENTION

Figure 2:
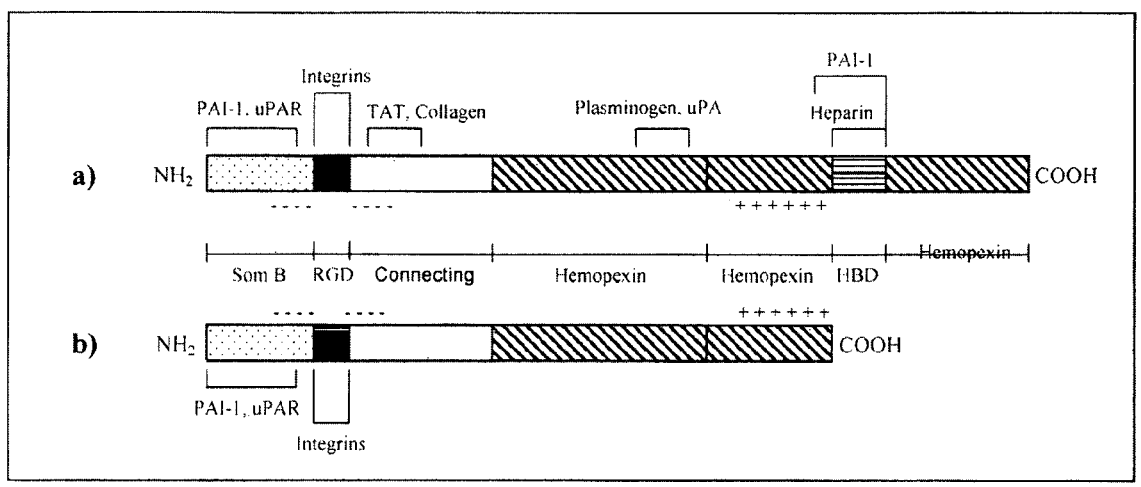
FIG. 2. The structural relationship of (a) full-length VN (75 kDa) and (b) yolk VN (54 kDa) showing ligand binding sites. Both mammalian and avian serum VN have the same domain structure, however, there are differences in the amino acid sequence. Yolk VN (54 kDa) is a truncated form of these proteins. The abbreviations used are: Som B, Somatomedin B; Connecting, Connecting domain; Hemopexin, Hemopexin-like repeat; HBD, Heparin binding domain; PAI-1, plasminogen activator inhibitor-1; uPAR, urokinase plasminogen activator receptor; TAT, thrombin-antithrombin. III complex; uPA, urokinase plasminogen activator; − − − −, polyanionic region (basic region); + + +, polycationic region (acidic region).

The present invention has arisen from the discovery that protein complexes comprising KGF and VN bind and exert their biological effect on cell migration through the KGF receptor and the VN-binding integrin receptor expressed by responsive cells. More particularly, this dual binding event synergistically stimulates cell migration and/or proliferation.

Although not wishing to be bound by any particular theory, it is thought that a domain of VN which interacts with or binds KGF is the polyanionic region of VN corresponding to amino acids 53-64 of mature VN (SEQ ID NO:2).

This discovery has led the present inventors to provide an isolated protein complex that comprises at least the minimal domain or region of KGF capable of binding the KGF receptor in combination with the integrin-binding domain of VN. Even more particularly, a single, contiguous protein may be produced which comprises these domains.

Such protein complexes, in the form of a single synthetic protein, coordinately bind or co-ligate the KGF receptor and the VN-binding integrin receptor and are therefore useful agents for the promotion of cell migration and/or proliferation and wound healing. Analogously, prevention of the KGF receptor and the VN-binding integrin receptor co-ligation can be used to prevent cancer cell metastasis.

Throughout this specification, unless otherwise indicated, "comprise", "comprises" and "comprising" are used inclusively rather than exclusively, so that a stated integer or group of integers may include one or more other non-stated integers or groups of integers.

In the particular context of keratinocyte growth factor receptor-binding domains and integrin-binding domains, such a domain will comprise an amino acid sequence of the domain, together with other, additional amino acids as desired.

It will be understood also that such a domain may "consist essentially of" the amino acid sequence of the domain, together with no more than ten, preferably no more than five or even more preferably no more than four, three, two, or one additional amino acids.

It will be understood also that such a domain may "consist of" the amino acid sequence of the domain, in the absence of any additional amino acids.

For the purposes of this invention, by "isolated" is meant material that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated material may be in native, chemical synthetic or recombinant form.

As used herein, by "synthetic" is meant not naturally occurring but made through human technical intervention. In the context of synthetic proteins and nucleic acids, this encompasses molecules produced by recombinant, chemical synthetic or combinatorial techniques as are well understood in the art.

By "protein" is meant an amino acid polymer. The amino acids may be natural or non-natural amino acids, D- or L-amino acids as are well understood in the art. The term "protein" also includes and encompasses such terms as "glycoprotein", "lipoprotein" and the like, as are commonly used in the art.

A "peptide" is a protein having less than fifty (50) amino acids.

A "polypeptide" is a protein having fifty (50) or more amino acids.

As hereinbefore described, the present invention provides, in one particular aspect, an isolated protein complex in the form of a synthetic chimeric protein comprising an amino acid sequence of:

(i) a keratinocyte growth factor or at least a domain of a keratinocyte growth factor which is capable of binding a keratinocyte growth factor receptor; and (ii) vitronectin, or at least an integrin-binding domain of vitronectin.

As used herein, a "chimeric protein" comprises a contiguous sequence of amino acids derived from an integrin receptor-binding domain of vitronectin and a keratinocyte growth factor or at least a receptor-binding domain of a keratinocyte growth factor.

As used herein, "keratinocyte growth factor" is a biologically active protein that is capable of regulating cell growth, differentiation, survival and/or migration in vitro and/or in vivo (Marchese et al., 1990, J. Cell Physiol. 144:326-32; UniProtKB/Swiss-Prot: #P21781, mature protein comprises amino acid residues 32-194 of the complete sequence).

Isolated protein complexes in the form of synthetic chimeric proteins of the invention comprise a keratinocyte growth factor or at least a domain of a keratinocyte growth factor which is capable of binding a keratinocyte growth factor receptor.

In this context, by "domain" is meant at least that portion of region of a keratinocyte growth factor that is capable of binding a keratinocyte growth factor receptor. Typically, although not exclusively, the keratinocyte growth factor receptor is expressed by a cell and binding or ligation of the keratinocyte growth factor receptor by the at least a domain of a keratinocyte growth factor elicits a cellular response such as cell growth, differentiation, survival and/or migration.

It will also be understood that another component of isolated protein complexes in the form of synthetic chimeric proteins of the invention is at least an integrin-binding domain of vitronectin.

Preferably, the integrin receptor is an $\alpha_v$ integrin.

More preferably, the integrin receptor is an $\alpha_v\beta_3$ integrin or $\alpha_v\beta_5$ integrin.

Although not wishing to be bound by any particular theory, it is proposed that synthetic chimeric proteins are able to co-ligate and co-activate a receptor for keratinocyte growth factor and an integrin receptor for VN to thereby stimulate, induce, augment, or otherwise promote cell growth, differentiation, survival and/or cell migration.

An advantage of chimeric proteins according to the invention is that they are readily produced by chemical synthetic or recombinant means and are expected to be more stable in vivo, as they do not rely on maintaining the protein-protein interactions that are required in non-covalent oligo-protein complexes.

The present invention contemplates embodiments of synthetic chimeric proteins that do not include the C-terminal heparin binding domain (HBD) and/or the polyanionic region of VN. By "C-terminal HBD" is meant residues 347-459 of the mature VN sequence (SEQ ID NO:2). Xu et al. (2001, Proteins 44:312-20) have argued that VN contains a second HBD in its central region. The present invention does not contemplate this alleged HBD.

With regard to VN proteins and amino acid sequences thereof that do not include the C-terminal. HBD and/or the polyanionic region, these may be naturally occurring proteins such as the 54 kD chicken yolk VN" (lacking a C-terminal HBD) or may be engineered by deletion, mutation or truncation of a VN protein or amino acid sequence so that the C-terminal HBD and/or the polyanionic region are absent or at least substantially non-functional.

Techniques such as proteolytic digestion and site directed mutagenesis may be utilized for this purpose, as are well understood in the art.

In particular embodiments, said at least an integrin-binding domain of VN has an amino acid sequence selected from the group consisting of:

(i) amino acid residues 1 to 459 of VN;
(ii) amino acid residues 1 to 379 of VN;
(iii) amino acid residues 1 to 346 of VN;
(iv) amino acid residues 1 to 311 of VN;
(v) amino acid residues 1 to 130 of VN;
(vi) amino acid residues 1 to 125 of VN;
(vii) amino acid residues 1 to 64 of VN; and
(viii) amino acid residues 1 to 52 of VN (all references are to the mature VN sequence (SEQ ID NO:2)).

Additional amino acid sequences which also may be included are selected from the group consisting of:
(ix) amino acid residues 65 to 459 of VN;
(x) amino acid residues 343 to 376 of VN;
(xi) amino acid residues 347 to 459 of VN; and
(xii) amino acid residues 347 to 379 of VN (all references are to the mature VN sequence (SEQ ID NO:2)).

The aforementioned sequences may be used in combination, for example amino acid residues 1 to 130 of VN and amino acid residues 347 to 459 of VN or amino acid residues 1 to 52 of VN and amino acid residues 65 to 459 of VN.

Particular, non-limiting example of chimeric proteins comprising KGF and VN are set forth in FIG. 3, and include:
(i) 1-459 VN:(Gly$_4$ Ser)$_4$:1-163 KGF:Gly$_4$ Ser Gly$_4$:6 His;
(ii) 1-311 VN:(Gly$_4$ Ser)$_4$:1-163 KGF:Gly$_4$ Ser Gly$_4$:6 His;
(iii) 1-125 VN:(Gly$_4$ Ser)$_4$:1-163 KGF:Gly$_4$ Ser Gly$_4$:6 His;
(iv) 1-64 VN:(Gly$_4$ Ser)$_4$:1-163 KGF:Gly$_4$ Ser Gly$_4$:6 His; and (v) 1-64 VN:(Gly$_4$ Ser)$_4$:343-376 VN:(Gly$_4$ Ser)$_4$:1-163 KGF:Gly$_4$ Ser Gly$_4$:6 His.

In other embodiments, the invention provides isolated protein complexes, such as in the form of synthetic chimeric proteins, comprising KGF and VN, or a fragment of VN that comprises at least an integrin-binding domain of VN.

In this context, by "fragment" is meant a domain, subsequence or portion of VN. The fragment preferably constitutes less than 500, less than 400, less than 300 or more preferably about 80-280 contiguous amino acids of a mature VN sequence.

The integrin binding domain of VN suitably comprises an RGD sequence (amino acids 45-47 of a mature VN sequence). Accordingly, in one particular embodiment, the synthetic chimera comprises a VN fragment comprising an RGD sequence.

Preferably, synthetic chimeric proteins as hereinbefore described further comprise a "linker sequence" located between and contiguous with a keratinocyte growth factor sequence and a VN amino acid sequence.

In one embodiment, said linker sequence comprises one or more glycine residues and one or more serine residues.

Particular examples of linker sequences may be selected from Gly$_4$ Ser (SEQ ID NO:4); Gly$_4$ Ser$_3$ (SEQ ID NO:5); (Gly$_4$ Ser)$_3$ (SEQ ID NO:6); and (Gly$_4$ Ser)$_4$ (SEQ ID NO:7), although without limitation thereto.

In another embodiment, the linker sequence includes a Plasmin Cleavage Recognition Site (Sakiyama-Elbert et al., 2001, FASEB 15:1300-02), such as according to the sequence:

```
Leu Ile Lys Met Lys Pro      (SEQ ID NO: 8)
```

In yet another embodiment, the linker sequence includes a Collagenase-3 Cleavage Recognition Site (Kim & Healy, 2003, Biomacromolecules 4:1214-23), such as according to the sequence:

```
Gln Pro Gln Gly Leu Ala Lys   (SEQ ID NO: 9)
```

The invention also extends to use of biologically-active fragments of the synthetic chimeric proteins of the invention and/or to use of biologically-active fragments of the keratinocyte growth factor receptor-binding domains and integrin binding domains exemplified herein.

In one embodiment, said "biologically-active fragment" has no less than 10%, preferably no less than 25%, more preferably no less than 50% and even more preferably no less than 75%, 80%, 85%, 90%, or 95% of a biological activity of a protein from which it is derived.

In another embodiment, said "biologically-active fragment" has no less than 10%, preferably no less than 25%, more preferably no less than 50% and even more preferably no less than 75%, 80%, 85%, 90%, or 95% of a contiguous amino acid sequence of a protein from which it is derived.

Also contemplated are variant protein complexes of the invention.

Typically, and in relation to proteins, a "variant" protein has one or more amino acids that have been replaced by different amino acids. It is well understood in the art that some amino acids may be changed to others with broadly similar properties without changing the nature of the activity of the protein (conservative substitutions).

It will be appreciated that one or more amino acid residues of a reference sequence, such as keratinocyte growth factor, receptor-binding domain of keratinocyte growth factor, an integrin-binding domain of VN, or one or more corresponding residues present in a synthetic chimeric protein, may be modified or deleted, or additional sequences added, without substantially altering the biological activity of the isolated protein complex of the invention.

Specific mutations in mature VN (SEQ ID NO:2) that are contemplated by the present invention include: (i) T50A; (ii) T57A; (iii) T50E; (iv) T57E; (v) S378E; (vi) S378A; and (v) S362E.

In one embodiment, a protein, variant shares at least 70%, preferably at least 80% and more preferably at least 90%, 95%, 98%, or 99% sequence identity with a reference amino acid sequence.

Preferably, sequence identify is measured over at least 60%, more preferably over at least 75%, more preferably over at least 90%, or more preferably over at least 95%, 98% or substantially the full length of the reference sequence.

In order to determine percent sequence identity, optimal alignment of amino acid and/or nucleotide sequences may be conducted by computerised implementations of algorithms (Geneworks program by Intelligenetics; GAP, BESTFIT, FASTA, and TFASTA in the Wisconsin Genetics Software Package Release 7.0, Genetics Computer Group, WI, USA) or by inspection and the best alignment (i.e., resulting in the highest percentage homology over the comparison window) generated by any of the various methods selected. Reference also may be made to the BLAST family of programs as for example disclosed by Altschul et al. (1997, Nucl. Acids Res. 25:3389-402).

In another example, "sequence identity" may be understood to mean the "match percentage" calculated by the DNASIS computer program (Version 2.5 for windows; available from Hitachi Software engineering Co., Ltd., South San Francisco, Calif., USA).

A detailed discussion of sequence analysis can be found in Unit 19.3 of CURRENT PROTOCOLS IN MOLECULAR BIOLOGY Eds. Ausubel et al. (John Wiley & Sons Inc NY, 1995-1999).

The invention also contemplates derivatives of a receptor-binding domain of keratinocyte growth factor, an integrin-binding domain of VN or an isolated protein complex comprising the same.

As used herein, "derivative" proteins of the invention have been altered, for example by addition, conjugation or complexing with other chemical moieties or by post-translational modification techniques as are well understood in the art "Additions" of amino acids may include fusion of the polypeptides or variants thereof with other polypeptides or proteins. The other protein may, by way of example, assist in the purification of the protein. For instance, these include a polyhistidine tag, maltose binding protein, green fluorescent protein (GFP), Protein A or glutathione S-transferase (GST).

Other derivatives contemplated by the invention include, but are not limited to, modification to side chains, incorporation of unnatural amino acids and/or their derivatives during peptide, polypeptide or protein synthesis and the use of crosslinkers and other methods which impose conformational constraints on the polypeptides, fragments and variants of the invention. Examples of side chain modifications contemplated by the present invention include modifications of amino groups such as by acylation with acetic anhydride; acylation of amino groups with succinic anhydride and tetrahydrophthalic anhydride; amidination with methylacetimidate; carbamoylation of amino groups with cyanate; pyridoxylation of lysine with pyridoxal-5-phosphate followed by reduction with $NaBH_4$; reductive alkylation by reaction with an aldehyde followed by reduction with $NaBH_4$; and trinitrobenzylation of amino groups with 2,4, 6-trinitrobenzene sulphonic acid (TNBS).

The carboxyl group may be modified by carbodiimide activation via O-acylisourea formation followed by subsequent derivitization, by way of example, to a corresponding amide.

The guanidine group of arginine residues may be modified by formation of heterocyclic condensation products with reagents such as 2,3-butanedione, phenylglyoxal and glyoxal.

Sulphydryl groups may be modified by methods such as performic acid oxidation to cysteic acid; formation of mercurial derivatives using 4-chloromercuriphenylsulphonic acid, 4-chloromercuribenzoate; 2-chloromercuri-4-nitrophenol, phenylmercury chloride, and other mercurials; formation of a mixed disulphides with other thiol compounds; reaction with maleimide, maleic anhydride or other substituted maleimide; carboxymethylation with iodoacetic acid or iodoacetamide; and carbamoylation with cyanate at alkaline pH.

Tryptophan residues may be modified, for example, by alkylation of the indole ring with 2-hydroxy-5-nitrobenzyl bromide or sulphonyl halides, or by oxidation with N-bromosuccinimide.

Tyrosine residues may be modified by nitration with tetranitromethane to form a 3-nitrotyrosine derivative.

The imidazole ring of a histidine residue may be modified by N-carbethoxylation with diethylpyrocarbonate or by alkylation with iodoacetic acid derivatives.

Examples of incorporating non-natural amino acids and derivatives during peptide synthesis include, but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine, and/or D-isomers of amino acids.

An example of methods suitable for chemical derivatization of proteins is provided in Chapter 15 of CURRENT PROTOCOLS IN PROTEIN SCIENCE Eds. Coligan et. al., John Wiley & Sons NY (1995-2001).

Isolated protein complexes, and individual protein components thereof, (inclusive of fragments, variants, derivatives, and homologs) may be prepared by any suitable procedure known to those, of skill in the art.

In one embodiment, proteins of the invention are produced by chemical synthesis. Chemical synthesis techniques are well known in the art, although the skilled person may refer to Chapter 18 of CURRENT PROTOCOLS IN PROTEIN SCIENCE Eds. Coligan et al., John Wiley & Sons NY (1995-2001) for examples of suitable methodology.

In another embodiment, proteins may be prepared as recombinant proteins.

While production of recombinant proteins is well known in the art, the skilled person may refer to standard protocols as for example described in Sambrook et al., MOLECULAR CLONING A Laboratory Manual (Cold Spring Harbor Press, 1989), in particular Sections 16 and 17; CURRENT PROTOCOLS IN MOLECULAR BIOLOGY Eds. Ausubel et al., (John Wiley & Sons, Inc. 1995-1999), in particular Chapters 10 and 16; and CURRENT PROTOCOLS IN PROTEIN SCIENCE Eds. Coligan et al., (John Wiley & Sons, Inc. 1995-1999), in particular Chapters 1, 5 and 6.

In one embodiment, a recombinant protein is produced by a method including the steps of:
 (i) preparing an expression construct which comprises a nucleic acid encoding said protein, operably linked to one or more regulatory nucleotide sequences in an expression vector;
 (ii) transfecting or transforming a host cell with the expression construct; and
 (iii) expressing the recombinant protein in said host cell.

An "expression vector" may be either a self-replicating extra-chromosomal vector such as a plasmid, or a vector that integrates into a host genome.

By "operably linked" or "operably connected" is meant that said regulatory nucleotide sequence(s) is/are positioned relative to the recombinant nucleic acid of the invention to initiate, regulate or otherwise control transcription of the nucleic acid, or translation of a protein encoded by the nucleic acid.

Regulatory nucleotide sequences will generally be appropriate for the host cell used for expression. Numerous types of appropriate expression vectors and suitable regulatory sequences are known in the art for a variety of host cells.

Typically, said one or more regulatory nucleotide sequences may include, but are not limited to, promoter sequences, leader or signal sequences, ribosomal binding sites, transcriptional start and termination sequences, translational start and termination sequences, splice donor/acceptor sequences, and enhancer or activator sequences.

Constitutive promoters (such as CMV, RSV, adenovirus, SV40, and human elongation factor promoters) and inducible/repressible promoters (such as tet-repressible promoters and IPTG-, metallothionine- or ecdysone-inducible promoters) are well known in the art and are contemplated by the invention. It will also be appreciated that promoters may be hybrid promoters that combine elements of more than one promoter.

The expression construct may also include a fusion partner (typically provided by the expression vector) so that the recombinant protein of the invention is expressed as a fusion polypeptide with said fusion partner. The main advantage of fusion partners is that they assist identification and/or purification of said fusion protein.

Well known examples of fusion partners include, but are not limited to, glutathione-S-transferase (GST), Fc portion of human IgG, maltose binding protein (MBP), and hexahistidine ($HIS_6$), which are particularly useful for isolation of the fusion protein by affinity chromatography. For the purposes of fusion protein purification by affinity chromatography, relevant matrices for affinity chromatography are glutathione-, amylose-, and nickel- or cobalt-conjugated resins respectively. Many such matrices are available in "kit" form, such as the QIAexpress™ system (Qiagen) useful with (HIS$_6$) fusion partners and the Pharmacia GST purification system.

In some cases, the fusion partners also have protease cleavage sites, such as for Factor X$_a$ or Thrombin, which allow the relevant protease to partially digest the fusion protein of the invention and thereby liberate the recombinant polypeptide of the invention therefrom. The liberated protein can then be isolated from the fusion partner by subsequent chromatographic separation.

Fusion partners according to the invention also include within their scope "epitope tags", which are usually short peptide sequences for which a specific antibody is available. Well known examples of epitope tags for which specific monoclonal antibodies are readily available include c-myc, haemagglutinin and FLAG tags.

Suitable host cells for expression may be prokaryotic or eukaryotic, such as *Escherichia coli* (DH5α for example), yeast cells, Sf9 cells utilized with a baculovirus expression system, CHO cells, COS, CV-1, NIH 3T3 and 293 cells, although without limitation thereto.

Expression constructs may also include one or more selection marker nucleotide sequences that confer transformed host cell resistance to a selection agent. Selection markers useful for the purposes of selection of transformed bacteria include bla, kanR and tetR while transformed eukaryotic cells may be selected by markers such as hygromycin, G418 and puromycin, although without limitation thereto.

With regard to introducing genetic material into host cells, the terms "transforming" and "transfecting" are used generally to describe introduction of genetic material into a host cell. There are many well known methods for introducing foreign genetic material into a host cell including, but not limited to, calcium phosphate precipitation, electroporation, delivery by lipofectamine, lipofectin and other lipophilic agents, calcium phosphate precipitation, DEAE-Dextran transfection, microparticle bombardment, microinjection, and protoplast fusion.

The invention provides an isolated nucleic acid that encodes a synthetic chimeric protein of the invention, including variants and homologs thereof.

The term "nucleic acid" as used herein designates single- or double-stranded mRNA, RNA, cRNA, RNAi, and DNA, inclusive of cDNA and genomic DNA and DNA-RNA hybrids.

A "polynucleotide" is a nucleic acid having eighty (80) or more contiguous nucleotides, while an "oligonucleotide" has less than eighty (80) contiguous nucleotides.

A "probe" may be a single or double-stranded oligonucleotide or polynucleotide, suitably labeled for the purpose of detecting complementary sequences in Northern or Southern blotting, for example.

A "primer" is usually a single-stranded oligonucleotide, preferably having 15-50 contiguous nucleotides, which is capable of annealing to a complementary nucleic acid "template" and being extended in a template-dependent fashion by the action of a DNA polymerase such as Taq polymerase, RNA-dependent DNA polymerase or Sequenase™.

Synthetic nucleic acids of the invention may be produced by chemical synthetic approaches or by recombinant methods that utilize nucleic acid sequence amplification techniques, or a combination thereof, as are well known in the art.

Chemically synthesized primers and oligonucleotides, synthesizers and associated technologies useful according to the present invention are typically available in most laboratories or may be purchased from commercial sources.

Suitable nucleic acid amplification techniques are well known to the skilled person, and include polymerase chain reaction (PCR) and ligase chain reaction (LCR) as for example described in Chapter 15 of CURRENT PROTOCOLS IN MOLECULAR BIOLOGY Eds. Ausubel et al. (John Wiley & Sons Inc NY, 1995-1999); strand displacement amplification (SDA) as for example described in U.S. Pat. No. 5,422,252; rolling circle replication (RCR) as for example described in Liu et al. (1996, J. Am. Chem. Soc. 118:1587-94), International application WO 92/01813 and International Application WO 97/19193; nucleic acid sequence-based amplification (NASBA) as for example described by Sooknanan et al. (1994, Biotechniques 17:1077-80); and Q-β replicase amplification as for example described by Tyagi et al. (1996, Proc. Natl. Acad. Sci. USA 93:5395-400), although without limitation thereto.

A preferred nucleic acid sequence amplification technique is PCR.

As used herein, an "amplification product" refers to a nucleic acid product generated by a nucleic acid amplification technique.

In producing and expressing nucleic acids of the invention, it will also be appreciated that advantage may be taken with respect to codon sequence redundancy, such that the nucleic acids exemplified herein may be readily modified without changing an amino acid sequence encoded thereby.

In particular embodiments, nucleic acids may be optimized according to preferred "codon usage" of a host cell to be used for recombinant expression, as is well known in the art. This can effectively "tailor" a nucleic acid for optimal expression in a particular organism, or cells thereof, where preferential codon usage affects protein expression.

Therefore, the invention includes synthetic nucleic acids that are homologous to the nucleic acids exemplified herein.

In one embodiment, nucleic acid homologs share at least 70%, preferably at least 80%, more preferably at least 90%, and even more preferably at least 95% sequence identity with a nucleic acid encoding any one of the synthetic chimeric protein constructs described herein.

Preferably, sequence identify is measured over at least 70%, more preferably at least 80%, even more preferably at least 90%, 95% or advantageously over substantially the full length of the encoding nucleic acid of the invention.

In another embodiment, nucleic acid homologs hybridize to a nucleic acid encoding any one of the synthetic chimeric protein constructs described herein under high stringency conditions.

"Hybridize and hybridization" is used herein to denote the pairing of at least partly complementary nucleotide sequences to produce a DNA-DNA, RNA-RNA or DNA-RNA duplex. Hybridized sequences occur through base-pairing between complementary purines and pyrimidines as is well known in the art.

In this regard, it will be appreciated that modified purines (for example, inosine, methylinosine and methyladenosine) and modified pyrimidines (thiouridine and methylcytosine) may also engage in base pairing.

"Stringency", as used herein, refers to temperature and ionic strength conditions, and presence or absence of certain organic solvents and/or detergents during hybridisation. The higher the stringency, the higher will be the required level of complementarity between hybridizing nucleotide sequences.

"Stringent conditions" designates those conditions under which only nucleic acid having a high frequency of complementary bases will hybridize.

Reference herein to high stringency conditions includes and encompasses:

(i) from at least about 31% v/v to at least about 50% v/v formamide and from at least about 0.01M to at least about 0.15 M salt for hybridisation at 42° C., and at least about 0.01M to at least about 0.15 M salt for washing at 42° C.;

(ii) 1% BSA, 1 mM EDTA, 0.5 M NaHPO$_4$ (pH 7.2), 7% SDS for hybridization at 65° C., and (a) 0.1×SSC, 0.1% SDS: or (b) 0.5% BSA, 1 mM EDTA, 40 mM NaHPO$_4$ (pH 7.2), 1% SDS for washing at a temperature in excess of 65° C. for about one hour; and (iii) 0.2×SSC, 0.1% SDS for washing at or above 68° C. for about 20 minutes.

In general, washing is carried out at $T_m$=69.3+0.41 (G+C) %−12° C. In general, the $T_m$ of a duplex DNA decreases by about 1° C. with every increase of 1% in the number of mismatched bases.

Notwithstanding the above, stringent conditions are well known in the art, such as described in Chapters 2.9 and 2.10 of CURRENT PROTOCOLS IN MOLECULAR BIOLOGY Eds. Ausubel et al. (John Wiley & Sons Inc NY, 1995-1999), and in particular at pages 2.9.1 through 2.9.20.

The invention also contemplates antibodies against a synthetic chimeric protein of the invention, inclusive of chimeric proteins, or fragments, variants and/or derivatives thereof. Antibodies of the invention may be polyclonal or monoclonal. Well-known protocols applicable to antibody production, purification and use may be found, for example, in Chapter 2 of Coligan et al., CURRENT PROTOCOLS IN IMMUNOLOGY (John Wiley & Sons NY, 1991-1994) and Harlow, E. & Lane, D. Antibodies: A Laboratory Manual, Cold Spring Harbor, Cold Spring Harbor Laboratory, 1988.

Generally, antibodies of the invention bind to or conjugate with a polypeptide, fragment, variant or derivative of the invention. For example, the antibodies may comprise polyclonal antibodies. Such antibodies may be prepared for example by injecting a polypeptide, fragment, variant or derivative of the invention into a production species, which may include mice or rabbits, to obtain polyclonal antisera. Methods of producing polyclonal antibodies are well known to those skilled in the art. Exemplary protocols which may be used are described for example in Coligan et al., CURRENT PROTOCOLS IN IMMUNOLOGY (John Wiley & Sons NY, 1991-1994), and in Harlow, E. & Lane, D. Antibodies: A Laboratory Manual, Cold Spring Harbor, Cold Spring Harbor Laboratory, 1988.

In lieu of the polyclonal antisera obtained in the production species, monoclonal antibodies may be produced using the standard method as for example, described by Köhler & Milstein (1975, Nature 256:495-97), or by more recent modifications thereof as, for example, described in Coligan et al., CURRENT PROTOCOLS IN IMMUNOLOGY (John Wiley & Sons NY, 1991-1994) by immortalizing spleen or other antibody producing cells derived from a production species which has been inoculated with one or more of the polypeptides, fragments, variants or derivatives of the invention.

The invention also includes within its scope antibodies which comprise Fc or Fab fragments of the polyclonal or monoclonal antibodies referred to above. Alternatively, the antibodies may comprise single chain. Fv antibodies (scFvs) against the proteins of the invention. Such scFvs may be prepared, for example, in accordance with the methods described respectively in U.S. Pat. No. 5,091,513, European Patent 239,400 or the article by Winter & Milstein (1991, Nature 349:293-99).

Labels may be associated with the antibody or antibody fragment.

The label may be selected from a group including a chromogen, a catalyst, an enzyme, a fluorophore, a chemiluminescent molecule, a lanthanide ion such as Europium (Eu$^{34}$), a radioisotope, and a direct visual label. In the case of a direct visual label, use may be made of a colloidal metallic or non-metallic particle, a dye particle, an enzyme or a substrate, an organic polymer, a latex particle, a liposome, or other vesicle containing a signal producing substance and the like.

A large number of enzymes useful as labels are disclosed in U.S. Pat. No. 4,366,241, U.S. Pat. No. 4,843,000 and U.S. Pat. No. 4,849,338. Enzyme labels useful in the present invention include alkaline phosphatase, horseradish peroxidase, luciferase, b-galactosidase, glucose oxidase, lysozyme, malate dehydrogenase and the like. The enzyme label may be used alone or in combination with a second enzyme in solution.

By way of example, the fluorophore may be fluorescein isothiocyanate (FITC), Oregon green, tetramethylrhodamine isothiocyanate (TRITE), allophycocyanin (APC) and R-Phycoerythrin (RPE), although without limitation thereto.

The invention also provides pharmaceutical compositions that comprise an isolated protein complex of the invention, inclusive of variants and derivatives thereof.

Such isolated protein complex may be in any form, inclusive of synthetic chimeric proteins of the invention, although without limitation thereto.

Pharmaceutical compositions of the invention may be used to promote or otherwise facilitate cell migration, tissue regeneration and wound healing. Alternatively, pharmaceutical compositions may be administered to prevent tumour metastasis by preventing or inhibiting tumour cell migration to a secondary site.

The composition may be used in therapeutic or prophylactic treatments as required. For example, pharmaceutical compositions may be applied in the form of therapeutic or cosmetic preparations for skin repair, wound healing, healing of burns and other dermatological treatments.

In this regard, pharmaceutical compositions may be administered in association with, or as a component of, a biomaterial, biopolymer, inorganic material such as hydroxyapatite or derivates thereof, surgical implant, prosthesis, wound or burn dressing, compress, bandage, or the like suitably impregnated, coated or otherwise comprising the pharmaceutical composition.

Suitably, the pharmaceutical composition comprises an appropriate pharmaceutically-acceptable carrier, diluent or excipient.

Preferably, the pharmaceutically-acceptable carrier, diluent or excipient is suitable for administration to mammals, and more preferably, to humans.

By "pharmaceutically-acceptable carrier, diluent or excipient" is meant a solid or liquid filler, diluent or encapsulating substance that may be safely used in systemic administration. Depending upon the particular route of administration, a variety of carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline and salts such as mineral acid salts including hydrochlorides, bromides and sulfates, organic acids such as acetates, propionates and malonates and pyrogen-free water.

A useful reference describing pharmaceutically acceptable carriers, diluents and excipients is Remington's Pharmaceutical Sciences (Mack Publishing Co. N.J. USA, 1991).

Any safe route of administration may be employed for providing a patient with the composition of the invention. For example, oral, rectal, parenteral, sublingual, buccal, intravenous, intra-articular, intra-muscular, intra-dermal; subcutaneous, inhalational, intraocular, intraperitoneal, intracerebroventricular, transdermal, and the like may be employed.

Dosage forms include tablets, dispersions, suspensions, injections, solutions, syrups, troches, capsules, suppositories, aerosols, transdermal patches, and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids, and certain cellulose derivatives such as hydroxypropylmethyl cellulose. In addition, the controlled release may be effected by using other polymer matrices, liposomes and/or microspheres.

The above compositions may be administered in a manner compatible with the dosage formulation, and in such amount as is pharmaceutically-effective. The dose administered to a patient, in the context of the present invention, should be sufficient to effect a beneficial response in a patient over an appropriate period of time. The quantity of agent(s) to be administered may depend on the subject to be treated, inclusive of the age, sex, weight and general health condition thereof, factors that will depend on the judgement of the practitioner.

With regard to pharmaceutical compositions for wound healing, particular reference is made to U.S. Pat. No. 5,936,064 and International Publication WO 99/62536.

Pharmaceutical compositions of the invention may also include expression vectors such as viral vectors such as vaccinia, and viral vectors useful in gene therapy. The latter include adenovirus and adenovirus-associated viruses (AAV) such as described in Braun-Falco et al. (1999, Gene Ther. 6:432-41), retroviral and lentiviral vectors such as described in Buchshacher et al. (2000, Blood 95:2499-504) and vectors derived from herpes simplex virus and cytomegalovirus. A general overview of viral vectors useful in endocrine gene therapy is provided in Stone et al. (2000, J. Endocrinol. 164:103-18).

The present invention may also utilize specific expression vectors which target gene expression to epidermal cells, such as described in U.S. Pat. No. 5,958,764 and for in vivo wound healing applications, such as described in U.S. Pat. No. 5,962,427.

The invention provides methods of treatment using isolated protein complexes, inclusive of synthetic chimeric proteins of the invention. These methods are particularly aimed at therapeutic and/or prophylactic treatment of mammals, and more particularly, humans.

However, therapeutic uses according to the invention may also be applicable to mammals such as domestic and companion animals, performance animals such as horses, camels and greyhounds, livestock, laboratory animals and animals used as sources of cells, organs and tissues for xenotransplantation.

The invention also contemplates methods of cosmetic treatment where isolated protein complexes, inclusive of synthetic chimeric proteins of the invention, are administered to improve or enhance skin quality or skin appearance.

Such treatments may include prevention or remediation of skin disorders such as psoriasis and hypertrophic scarring that result from aberrant skin cell proliferation.

Alternatively, methods of treatment are contemplated whereby tumour metastasis is prevented or inhibited by blocking tumour cell migration to a secondary site. In addition, methods of treating cancer by blocking cell proliferation also contemplated.

In particular embodiments, therapeutic and/or prophylactic treatments may utilize an isolated protein complex, inclusive of synthetic chimeric proteins of the invention, in association with, or as a component of, a biomaterial, biopolymer, inorganic material such as fluorohydroxyapatite, surgical implant, prosthesis, wound or burn dressing, compress, bandage, or the like suitably impregnated, coated or otherwise comprising the isolated protein complex.

Such methods include administration of pharmaceutical compositions as hereinbefore defined, and may be by way of microneedle injection into specific tissue sites, such as described in U.S. Pat. No. 6,090,790, topical creams, lotions or sealant dressings applied to wounds, burns or ulcers, such as described in U.S. Pat. No. 6,054,122 or implants which release the composition such as described in International Publication WO 99/47070.

Gene therapy is also applicable in this regard, such as according to methods set forth in U.S. Pat. No. 5,929,040 and U.S. Pat. No. 5,962,427.

There also exist methods by which skin cells can be genetically modified for the purpose of creating skin substitutes, such as by genetically engineering desired growth factor expression (Supp et al., 2000, J. Invest. Dermatol. 114:5-13). An example of a review of this field is provided in Bevan et al. (1999, Biotechnol. Gent. Eng. Rev. 16:231-56).

Also contemplated is "seeding" a recipient with transfected or transformed cells, such as described in International Publication WO 99/11789.

These methods can be used to stimulate cell migration and thereby facilitate or progress wound and burn healing, repair of skin lesions such as ulcers, tissue replacement and grafting such as by in vitro culturing of autologous skin, re-epithelialization of internal organs such as kidney and lung and repair of damaged nerve tissue.

Skin replacement therapy has become well known in the art, and may employ use of co-cultured epithelial/keratinocyte cell lines, for example as described in Kehe et al. (1999, Arch. Dermatol. Res. 291:600-05) or in vitro culture of primary (usually autologous) epidermal, dermal and/or keratinocyte cells. These techniques may also utilize engineered biomaterials and synthetic polymer "scaffolds".

Examples of reviews of the field in general are provided in Terskikh & Vasiliev (1999, Int. Rev. Cytol. 188:41-72) and Eaglestein & Falanga (1998, Cutis 62:1-8).

More particularly, the production of replacement oral mucosa useful in craniofacial surgery is described in Izumi al. (2000, J. Dent. Res. 79:798-805). Fetal keratinocytes and dermal fibroblasts can be expanded in vitro to produce skin for grafting to treat skin lesions, such as described in Fauza et al. (1998, J. Pediatr. Surg. 33:357-61), while skin substitutes from dermal and epidermal skin elements cultured in vitro on hyaluronic acid-derived biomaterials have been shown to be potentially useful in the treatment of burns (Zacehi et al., 1998, J. Biomed. Mater. Res. 40:187-94).

Polymer scaffolds are also contemplated for the purpose of facilitating replacement skin engineering, as for example described in Sheridan et al. (2000, J. Control Release 64:91-102) and Fauza et al. (1998, J. Pediatr. Surg. 33:357-61), as are microspheres as agents for the delivery of skin cells to wounds and burns (LaFrance & Armstrong, 1999, Tissue Eng. 5:153-70).

The invention contemplates use of isolated protein complexes, inclusive of synthetic chimeric, proteins of the invention, to identify, screen, design or otherwise produce agonists or antagonists of complexes comprising keratinocyte growth factor and vitronectin. Such agents may be a "mimetic". The term "mimetic" is used herein to refer to molecules that are designed to resemble particular functional regions of proteins or peptides, and includes within its scope the terms "agonist", "analogue" and "antagonist" as are well understood in the art.

In one embodiment, agonists are produced that mimic the binding of the keratinocyte growth factor receptors and VN receptors by KGF:VN complexes. Such molecules may have utility as stimulators of cell migration such as required for wound healing, skin regeneration and the like.

In another embodiment, antagonists are produced that prevent or inhibit the binding of the keratinocyte growth factor receptors and integrin receptors by KGF:VN complexes. Such molecules have utility as inhibitors of cell migration and/or cell proliferation: and thereby constitute useful anti-tumour agents and also in treatments of skin disorders such as psoriasis and hypertrophic scarring that result from aberrant cell proliferation.

The aforementioned mimetics, agonists, antagonists and analogues may be peptides, polypeptides or other organic molecules, preferably small organic molecules, with a desired biological activity and half-life.

Computer-assisted structural database searching is becoming increasingly utilized as a procedure for identifying mimetics. Database searching methods which, in principle, may be suitable for identifying mimetics, may be found in International Publication WO 94/18232 (directed to producing 111V antigen mimetics), U.S. Pat. No. 5,752,019 and International Publication WO 97/41526 (directed to identifying EPO mimetics).

Other methods include a variety of biophysical techniques which identify molecular interactions. These allow for the screening of candidate molecules according to whether said candidate molecule affects formation of KGF:VN complexes, for example. Methods applicable to potentially useful techniques such as competitive radioligand binding assays (see, Upton et al., 1999, Endocrinology 140:2928-31 for a relevant method), analytical ultracentrifugation, microcalorimetry, surface plasmon resonance; and optical biosensor-based methods are provided in Chapter 20 of CURRENT PROTOCOLS IN PROTEIN SCIENCE Eds. Coligan et al., (John Wiley & Sons, 1997).

So that the present invention may be more readily understood and put into practical effect, the skilled person is referred to the following non-limiting examples.

EXAMPLES

Example 1

KGF:VN Chimeras Stimulate Cell Migration and Proliferation

Figure 4:
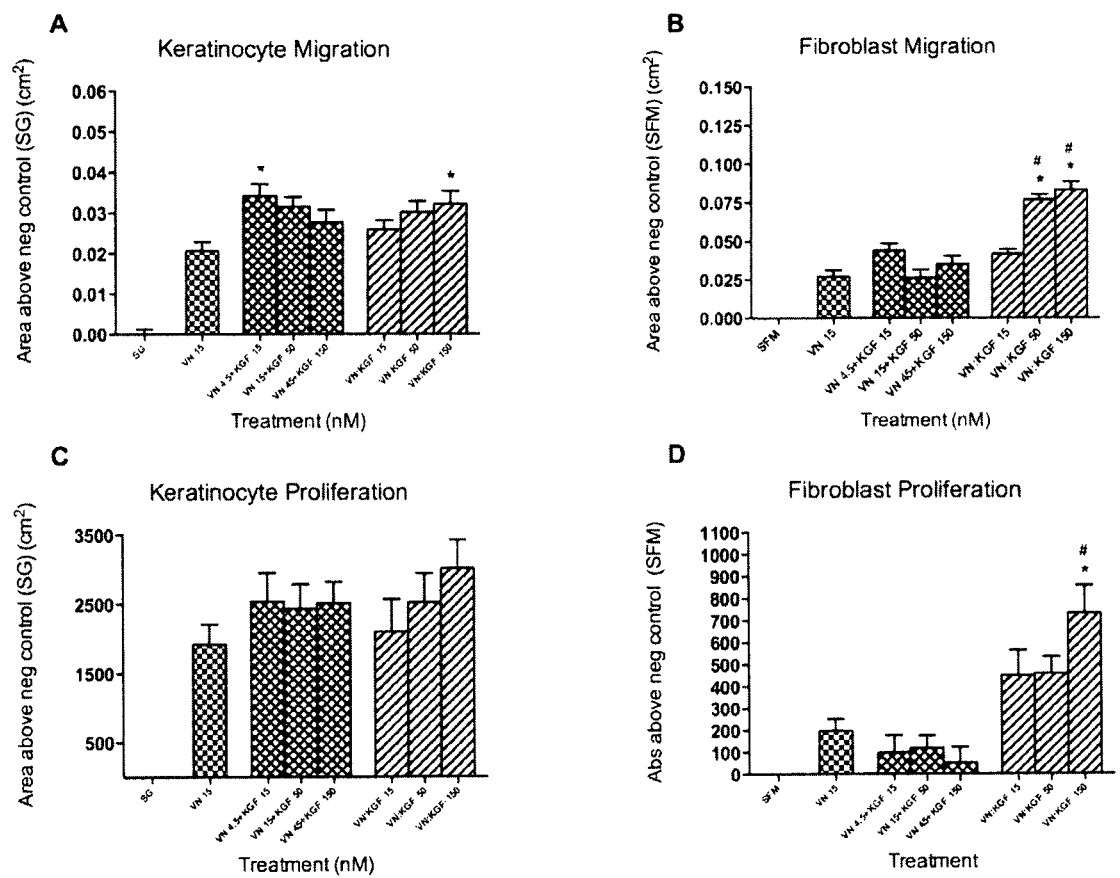
FIG. 4. (A) A VN:KGF chimeric protein stimulates primary keratinocyte cell migration. Migration of isolated skin keratinocyte cells seeded within the inner chamber of a seeding insert which was removed to allow outward migration, in response to the culture well being coated with a VN:KGF chimera and controls. Each bar represents the average area (+/−SEM) of cell coverage after 24 hours incubation and are obtained from at least three replicate experiments in which treatments were analysed in triplicate wells. (B) A VN:KGF chimeric protein stimulates primary fibroblast cell migration. Migration of isolated skin fibroblast cells seeded within the inner chamber of a seeding insert which was removed to allow outward migration, in response to the culture well being coated with a VN:KGF chimera and controls. Each bar represents the average area (+/−SEM) of cell coverage after 24 hours incubation and are obtained from at least three replicate experiments in which treatments were analysed in triplicate wells. (C) A VN:KGF chimeric protein stimulates primary keratinocyte cell proliferation. Proliferation of isolated skin keratinocyte cells in response to the culture well being coated with a VN:KGF chimera and controls. Each bar represents the average absorbance (+/−SEM) of DNA-binding GR dye (representative of cell number) after 72 hours incubation and are obtained from at least three replicate experiments in which treatments were analysed in triplicate wells. (D) A VN:KGF chimeric protein stimulates primary fibroblast cell proliferation. Proliferation of isolated skin fibroblast cells in response to the culture well being coated with a VN:KGF chimera and controls. Each bar represents the average absorbance (+/−SEM) of DNA-binding GR dye (representative of cell number) after 24 hours incubation and are obtained from at least three replicate experiments in which treatments were analysed in triplicate wells.

Isolated human keratinocyte and fibroblast cells (P1 and P3 respectively) were applied to the inner chamber of a seeding ring in culture wells pre-treated with varying doses of a VN:KGF chimera. and controls. After a 4-hour period of attachment, the seeding ring was removed and cells were allowed to migrate outward in response to the pre-bound treatments over "a period of" 24 hours for keratinocytes and 48 hours for fibroblasts. Cell assay data were pooled from at least 3 separate experiments, each with triplicate independent tests with results expressed as percentage above SG/SFM (negative control) and shown in FIGS. 4A and 4B. Error bars indicate SEM. SG=Stripped Greens media, SFM=Serum-free media (both are negative controls). With reference to experiments utilizing isolated human skin keratinocytes, the VN:KGF chimera demonstrated functional equivalence to equimolar combinations of individual components (VN+KGF), indicating proper protein expression, purification and processing. Experiments testing the response of isolated skin fibroblasts indicated that the VN:KGF chimera induced cell migration significantly ($p=<0.05$) above equimolar combinations of individual components (VN+KGF).

In order to assess the proliferation inducing potential of the VN:KGF chimera, isolated human keratinocyte and fibroblast cells (P1 and P3 respectively) were seeded into wells pre-treated with varying doses of VN:KGF chimera, and controls at a density of 15,000 cells/cm$^2$. The cells were allowed to proliferate over 72 and 48 hours for keratinocytes and fibroblasts respectively after which the culture media was removed and the culture plates snap frozen at $-80°$ C. Upon thawing of the plates, a mixture of cell lysis and GR-dye (Invitrogen, CYQUANT kit) was added to each well and incubated at room temperature for 5 minutes. The plates were then interrogated for fluorescence by excitation at 485 nm and absorbance was read at 520 nm. Cell assay data were pooled from at least 3 separate experiments; each with triplicate independent tests with results expressed as percentage above SG/SFM (negative control) and shown in FIGS. 4C and 4D. Error bars indicate SEM. SG=Stripped Greens media. SFM=Serum-free media (both are negative controls). Experiments testing proliferation in isolated human skin keratinocytes demonstrated that the VN:KGF chimera functioned in equivalence to equimolar combinations of individual components (VN+KGF). Proliferation experiments utilising isolated skin fibroblasts indicated that the VN:KGF chimera (150 nM) induced cell proliferation significantly ($p=<0.05$) above equimolar combinations of individual components and tetrameric VN:IGFBP-3:IGF-1:EGF complex.

Example 2

VN:KGF Signaling

In order to assess the impact of VN:KGF chimeric proteins on ERK 1/2 and AKT signaling pathways, the CELISA (Millipore) kit was used. Briefly, 20,000 primary keratinocytes or 10,000 primary fibroblasts were seeded into the wells of a 96 well black-bottomed fluorescence plate and allowed to grow overnight at $37°$ C. The cells were then washed 2× with serum free media (SFM) and incubated in SFM overnight to serum starve the cells. After approximately 16 hours, serum starvation media was replaced with 100 µL of protein treatments as follows: VN only (15 nM, equal to 1125 ng/mL), VN (15 nM, equal to 1125 ng/mL) and KGF (50 nM, equal to 820.4 ng/mL) and VN:KGF (50 nM, equal to 1318.9 ng/mL). Cells were exposed to protein treatments for time points of 10 minutes, 30 minutes and 60 minutes, after which treatment solutions were replaced with 4% formaldehyde in TBS to fix the cells. Wells were then interrogated for levels of activated. (phosphorylated) ERK 1/2 and AKT as a proportion of total ERK 1/2 and AKT respectively using antibody-based (ELISA) methods following the manufacturers instructions.

Figure 5:
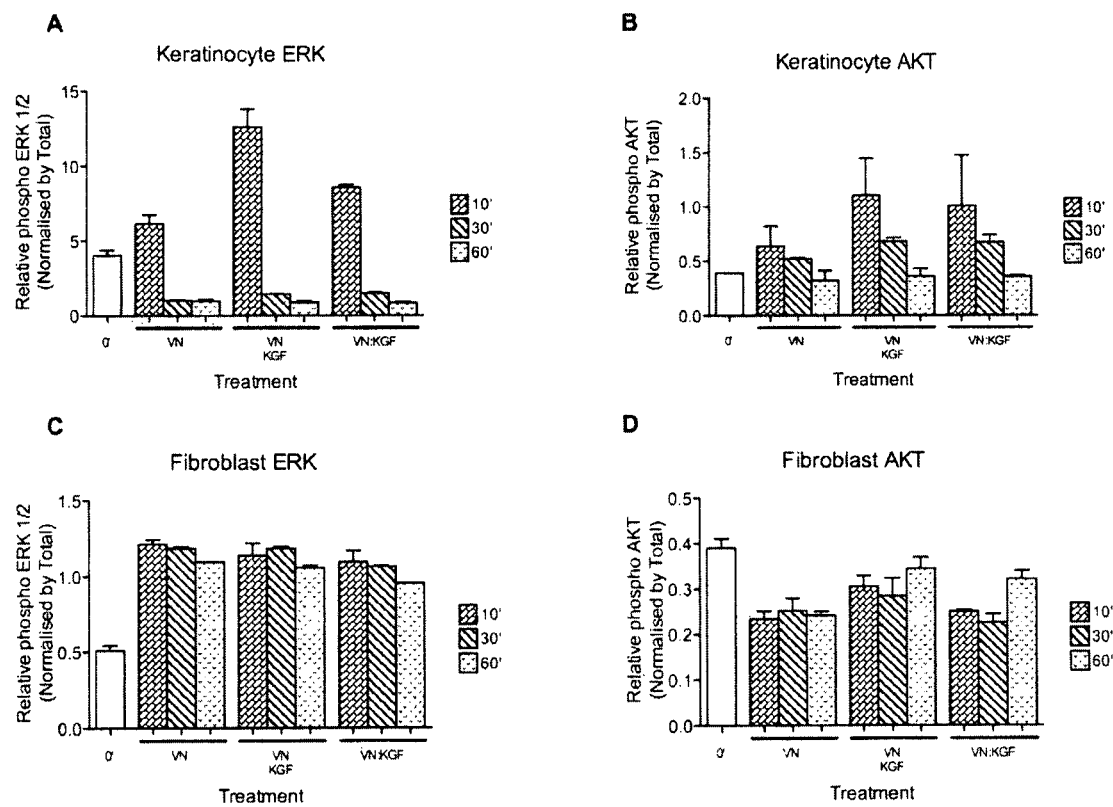
FIG. 5. Primary keratinocyte and fibroblast signaling responses to VN:KGF chimeric proteins and controls. VN:KGF chimeric proteins promote similar levels of realtive activation of ERK1/2 and AKT signaling pathways as respective controls: (A) keratinocyte ERK1/2; (B) keratinocyte AKT; (C) fibroblast ERK1/2; (D) fibroblast AKT.

Chimeric treatments promote similar levels of relative activation and demonstrate similar trends over time as respective controls (FIG. 5).

Example 3

Synthetic Chimeric Vitronectin Keratinocyte Growth Factor Proteins

Provided herein are examples of synthetic chimeric proteins of the invention, in the form of VN:KGF chimeras.

The synthetic chimeric proteins include any full-length or truncated forms of VN fused with keratinocyte growth factor, with or without amino acid residue modifications. In addition, VN and the keratinocyte growth factor may be fused with or without the various peptide linkers.

A series of chimeric expression constructs are designed in which various lengths of the VN protein are linked to the full-length mature KGF protein, or at least a domain of the KGF protein capable of binding a keratinocyte growth factor receptor. In each case, the VN segments are preferably linked to the KGF sequence via a linker, for example, a $Gly_4$ Ser (SEQ ID NO:4) linker, a $Gly_4$ $Ser_3$ (SEQ ID NO:5) linker, a ($Gly_4$ Ser); (SEQ ID NO:6) linker, or a ($Gly_4$ Ser)$_4$ (SEQ ID NO:7) linker.

Exemplary synthetic chimeric proteins include, but are not limited to:
A) 1-459VN:[Linker; e.g., $(G_4S)_4$]: 1-163KGF: [Linker; e.g., $G_4SG_4$]:6H
B) 1-311VN:[Linker; e.g., $(G_4S)_4$]:1-163KGF:[Linker; e.g., $G_4SG_4$]:6H
C) 1-125VN:[Linker; e.g., $(G_4S)_4$]:1-163KGF:[Linker; e.g., $G_4SG_4$]:6H
D) 1-64VN:[Linker; e.g., $(G_4S)_4$]:1-163KGF:[Linker; e.g., $G_4SG_4$]:6H
E) 1-64VN:[Linker; e.g., $(G_4S)_4$]:343-376VN:[Linker; e.g., $(G_4S)_4$]:1-163KGF:[Linker; e.g., $G_4SG_4$]:6H.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein are incorporated herein by reference.

---

What is claimed is:

1. An isolated protein complex in the form of a synthetic chimeric protein, the synthetic chimeric protein comprising:
   at least one protein domain of KGF capable of binding a keratinocyte growth factor receptor; and
   at least one protein domain of vitronectin (VN) comprising at least one integrin-binding domain;
   wherein the synthetic chimeric protein comprises an amino acid sequence comprising at least one of the following:

(i)
(SEQ ID NO: 10)
1-459 VN:(Gly$_4$ Ser)$_4$:1-163 KGF:Gly$_4$ Ser Gly$_4$:6 His, (ii)
(SEQ ID NO: 11)
1-311 VN:(Gly$_4$ Ser)$_4$:1-163 KGF:Gly$_4$ Ser Gly$_4$:6 His, (iii)
(SEQ ID NO: 12)
1-125 VN:(Gly$_4$ Ser)$_4$:1-163 KGF:Gly$_4$ Ser Gly$_4$:6 His,
or (iv)
(SEQ ID NO: 14)
1-64 VN:(Gly$_4$ Ser)$_4$:343-376 VN:(Gly$_4$ Ser)$_4$:1-163 KGF:Gly$_4$ Ser Gly$_4$:6 His.

2. An isolated nucleic acid molecule encoding the isolated protein complex of claim 1.

3. A genetic construct comprising the isolated nucleic acid molecule of claim 2 operably linked to one or more nucleic acid molecules comprising one or more regulatory nucleotide sequences in a vector.

4. The genetic construct of claim 3, wherein the genetic construct is an expression construct, and wherein the isolated nucleic acid molecule is operably linked to a heterologous promoter.

5. An isolated host cell comprising the genetic construct of claim 3.

6. A genetic construct comprising the isolated nucleic acid molecule of claim 2 operably linked to one or more nucleic acid molecules encoding one or more fusion polypeptides.

7. The genetic construct of claim 6, wherein the one or more fusion polypeptides is one or more of glutathione-S-transferase (GST), Fc portion of human IgG, maltose binding protein (MBP), hexahistidine (HIS$_6$), and c-myc, haemagglutinin and FLAG tags.

8. A pharmaceutical composition comprising the isolated protein complex of claim 1 and a pharmaceutically-acceptable carrier, diluent or excipient.

9. The pharmaceutical composition of claim 8, wherein the composition comprises a controlled release coating comprising one or more of a hydrophobic polymer, an acrylic resin, a wax, an aliphatic alcohol, a polylactic or polyglycolic acid, and a cellulose derivative.

10. A surgical implant, scaffold or prosthesis comprising the isolated protein complex of claim 1.

11. The surgical implant, scaffold or prosthesis of claim 10, wherein the isolated protein complex of claim 1 impregnates or coats the surgical implant, scaffold or prosthesis.

12. A wound or burn dressing comprising the isolated protein complex of claim 1.

13. A method of treating dermatological wounds in a subject, comprising a step of using the isolated protein complex of claim 1 to bind both a keratinocyte growth factor receptor and an integrin receptor expressed by a cell for inducing, augmenting or promoting at least one of migration and proliferation of said cell thereby treating the dermatological wounds in the subject.

14. The method of claim 13, wherein the isolated protein complex is administered to the subject to promote cell migration and/or proliferation in situ.

15. The method of claim 14, wherein the subject is a human.

16. The method of claim 13, comprising inducing, augmenting or promoting at least one of epithelial cell migration and proliferation as part of therapeutic treatment to facilitate wound healing in situ or to reduce the onset of a dermatologic disorder.

17. The method of claim 16, wherein the dermatological disorder comprises a hyperproliferative dermatological disorder.

18. The method of claim 13, comprising administering the isolated protein complex to one or more cells or tissues in vitro.

* * * * *

UNITED STATES PATENT AND TRADEMARK OFFICE
CERTIFICATE OF CORRECTION

PATENT NO. : 9,562,086 B2
APPLICATION NO. : 13/701472
DATED : February 7, 2017
INVENTOR(S) : Upton et al.

It is certified that error appears in the above-identified patent and that said Letters Patent is hereby corrected as shown below:

On the Title Page

Please change the Assignee to:
TISSUE THERAPIES LIMITED        BRISBANE, QUEENSLAND, AU Signed and Sealed this
First Day of May, 2018

Andrei Iancu
*Director of the United States Patent and Trademark Office*

SEQUENCE LISTING

```
<160> NUMBER OF SEQ ID NOS: 14

<210> SEQ ID NO 1
<211> LENGTH: 478
<212> TYPE: PRT
<213> ORGANISM: Homo sapiens

<400> SEQUENCE: 1

Met Ala Pro Leu Arg Pro Leu Leu Ile Leu Ala Leu Leu Ala Trp Val
1               5                   10                  15

Ala Leu Ala Asp Gln Glu Ser Cys Lys Gly Arg Cys Thr Glu Gly Phe
            20                  25                  30

Asn Val Asp Lys Lys Cys Gln Cys Asp Glu Leu Cys Ser Tyr Tyr Gln
        35                  40                  45

Ser Cys Cys Thr Asp Tyr Thr Ala Glu Cys Lys Pro Gln Val Thr Arg
    50                  55                  60

Gly Asp Val Phe Thr Met Pro Glu Asp Glu Tyr Thr Val Tyr Asp Asp
65                  70                  75                  80

Gly Glu Glu Lys Asn Asn Ala Thr Val His Glu Gln Val Gly Gly Pro
                85                  90                  95

Ser Leu Thr Ser Asp Leu Gln Ala Gln Ser Lys Gly Asn Pro Glu Gln
            100                 105                 110

Thr Pro Val Leu Lys Pro Glu Glu Glu Ala Pro Ala Pro Glu Val Gly
        115                 120                 125

Ala Ser Lys Pro Glu Gly Ile Asp Ser Arg Pro Glu Thr Leu His Pro
    130                 135                 140

Gly Arg Pro Gln Pro Pro Ala Glu Glu Glu Leu Cys Ser Gly Lys Pro
145                 150                 155                 160

Phe Asp Ala Phe Thr Asp Leu Lys Asn Gly Ser Leu Phe Ala Phe Arg
                165                 170                 175

Gly Gln Tyr Cys Tyr Glu Leu Asp Glu Lys Ala Val Arg Pro Gly Tyr
            180                 185                 190
```

```
Pro Lys Leu Ile Arg Asp Val Trp Gly Ile Glu Gly Pro Ile Asp Ala
        195                 200                 205

Ala Phe Thr Arg Ile Asn Cys Gln Gly Lys Thr Tyr Leu Phe Lys Gly
210                 215                 220

Ser Gln Tyr Trp Arg Phe Glu Asp Gly Val Leu Asp Pro Asp Tyr Pro
225                 230                 235                 240

Arg Asn Ile Ser Asp Gly Phe Asp Gly Ile Pro Asp Asn Val Asp Ala
                245                 250                 255

Ala Leu Ala Leu Pro Ala His Ser Tyr Ser Gly Arg Glu Arg Val Tyr
            260                 265                 270

Phe Phe Lys Gly Lys Gln Tyr Trp Glu Tyr Gln Phe Gln His Gln Pro
        275                 280                 285

Ser Gln Glu Glu Cys Glu Gly Ser Ser Leu Ser Ala Val Phe Glu His
    290                 295                 300

Phe Ala Met Met Gln Arg Asp Ser Trp Glu Asp Ile Phe Glu Leu Leu
305                 310                 315                 320

Phe Trp Gly Arg Thr Ser Ala Gly Thr Arg Gln Pro Gln Phe Ile Ser
                325                 330                 335

Arg Asp Trp His Gly Val Pro Gly Gln Val Asp Ala Ala Met Ala Gly
            340                 345                 350

Arg Ile Tyr Ile Ser Gly Met Ala Pro Arg Pro Ser Leu Ala Lys Lys
        355                 360                 365

Gln Arg Phe Arg His Arg Asn Arg Lys Gly Tyr Ser Gln Arg Gly
    370                 375                 380

His Ser Arg Gly Arg Asn Gln Asn Ser Arg Arg Pro Ser Arg Ala Met
385                 390                 395                 400

Trp Leu Ser Leu Phe Ser Ser Glu Glu Ser Asn Leu Gly Ala Asn Asn
                405                 410                 415

Tyr Asp Asp Tyr Arg Met Asp Trp Leu Val Pro Ala Thr Cys Glu Pro
            420                 425                 430

Ile Gln Ser Val Phe Phe Phe Ser Gly Asp Lys Tyr Tyr Arg Val Asn
        435                 440                 445

Leu Arg Thr Arg Arg Val Asp Thr Val Asp Pro Pro Tyr Pro Arg Ser
    450                 455                 460

Ile Ala Gln Tyr Trp Leu Gly Cys Pro Ala Pro Gly His Leu
465                 470                 475

<210> SEQ ID NO 2
<211> LENGTH: 459
<212> TYPE: PRT
<213> ORGANISM: Homo sapiens

<400> SEQUENCE: 2

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
                20                  25                  30

Thr Asp Tyr Thr Ala Glu Cys Lys Pro Gln Val Thr Arg Gly Asp Val
            35                  40                  45

Phe Thr Met Pro Glu Asp Glu Tyr Thr Val Tyr Asp Asp Gly Glu Glu
        50                  55                  60

Lys Asn Asn Ala Thr Val His Glu Gln Val Gly Gly Pro Ser Leu Thr
65                  70                  75                  80

Ser Asp Leu Gln Ala Gln Ser Lys Gly Asn Pro Glu Gln Thr Pro Val
                85                  90                  95
```

-continued

Leu Lys Pro Glu Glu Ala Pro Ala Pro Glu Val Gly Ala Ser Lys
            100                 105                 110

Pro Glu Gly Ile Asp Ser Arg Pro Glu Thr Leu His Pro Gly Arg Pro
        115                 120                 125

Gln Pro Pro Ala Glu Glu Leu Cys Ser Gly Lys Pro Phe Asp Ala
        130                 135                 140

Phe Thr Asp Leu Lys Asn Gly Ser Leu Phe Ala Phe Arg Gly Gln Tyr
145                 150                 155                 160

Cys Tyr Glu Leu Asp Glu Lys Ala Val Arg Pro Gly Tyr Pro Lys Leu
                165                 170                 175

Ile Arg Asp Val Trp Gly Ile Glu Gly Pro Ile Asp Ala Ala Phe Thr
                180                 185                 190

Arg Ile Asn Cys Gln Gly Lys Thr Tyr Leu Phe Lys Gly Ser Gln Tyr
                195                 200                 205

Trp Arg Phe Glu Asp Gly Val Leu Asp Pro Asp Tyr Pro Arg Asn Ile
            210                 215                 220

Ser Asp Gly Phe Asp Gly Ile Pro Asp Asn Val Asp Ala Ala Leu Ala
225                 230                 235                 240

Leu Pro Ala His Ser Tyr Ser Gly Arg Glu Arg Val Tyr Phe Phe Lys
                245                 250                 255

Gly Lys Gln Tyr Trp Glu Tyr Gln Phe Gln His Gln Pro Ser Gln Glu
                260                 265                 270

Glu Cys Glu Gly Ser Ser Leu Ser Ala Val Phe Glu His Phe Ala Met
                275                 280                 285

Met Gln Arg Asp Ser Trp Glu Asp Ile Phe Glu Leu Leu Phe Trp Gly
            290                 295                 300

Arg Thr Ser Ala Gly Thr Arg Gln Pro Gln Phe Ile Ser Arg Asp Trp
305                 310                 315                 320

His Gly Val Pro Gly Gln Val Asp Ala Ala Met Ala Gly Arg Ile Tyr
                325                 330                 335

Ile Ser Gly Met Ala Pro Arg Pro Ser Leu Ala Lys Lys Gln Arg Phe
                340                 345                 350

Arg His Arg Asn Arg Lys Gly Tyr Arg Ser Gln Arg Gly His Ser Arg
            355                 360                 365

Gly Arg Asn Gln Asn Ser Arg Arg Pro Ser Arg Ala Thr Trp Leu Ser
            370                 375                 380

Leu Phe Ser Ser Glu Glu Ser Asn Leu Gly Ala Asn Asn Tyr Asp Asp
385                 390                 395                 400

Tyr Arg Met Asp Trp Leu Val Pro Ala Thr Cys Glu Pro Ile Gln Ser
                405                 410                 415

Val Phe Phe Phe Ser Gly Asp Lys Tyr Tyr Arg Val Asn Leu Arg Thr
                420                 425                 430

Arg Arg Val Asp Thr Val Asp Pro Pro Tyr Pro Arg Ser Ile Ala Gln
            435                 440                 445

Tyr Trp Leu Gly Cys Pro Ala Pro Gly His Leu
            450                 455

<210> SEQ ID NO 3
<211> LENGTH: 163
<212> TYPE: PRT
<213> ORGANISM: Homo sapiens

<400> SEQUENCE: 3

```
Cys Asn Asp Met Thr Pro Glu Gln Met Ala Thr Asn Val Asn Cys Ser
1               5                   10                  15
Ser Pro Glu Arg His Thr Arg Ser Tyr Asp Tyr Met Glu Gly Gly Asp
                20                  25                  30
Ile Arg Val Arg Arg Leu Phe Cys Arg Thr Gln Trp Tyr Leu Arg Ile
            35                  40                  45
Asp Lys Arg Gly Lys Val Lys Gly Thr Gln Glu Met Lys Asn Asn Tyr
        50                  55                  60
Asn Ile Met Glu Ile Arg Thr Val Ala Val Gly Ile Val Ala Ile Lys
65                  70                  75                  80
Gly Val Glu Ser Glu Phe Tyr Leu Ala Met Asn Lys Glu Gly Lys Leu
                85                  90                  95
Tyr Ala Lys Lys Glu Cys Asn Glu Asp Cys Asn Phe Lys Glu Leu Ile
                100                 105                 110
Leu Glu Asn His Tyr Asn Thr Tyr Ala Ser Ala Lys Trp Thr His Asn
            115                 120                 125
Gly Gly Glu Met Phe Val Ala Leu Asn Gln Lys Gly Ile Pro Val Arg
        130                 135                 140
Gly Lys Lys Thr Lys Lys Glu Gln Lys Thr Ala His Phe Leu Pro Met
145                 150                 155                 160
Ala Ile Thr
```

<210> SEQ ID NO 4
<211> LENGTH: 5
<212> TYPE: PRT
<213> ORGANISM: Artificial Sequence
<220> FEATURE:
<223> OTHER INFORMATION: Synthetic Linker

<400> SEQUENCE: 4

```
Gly Gly Gly Gly Ser
1               5
```

<210> SEQ ID NO 5
<211> LENGTH: 7
<212> TYPE: PRT
<213> ORGANISM: Artificial Sequence
<220> FEATURE:
<223> OTHER INFORMATION: Synthetic Linker

<400> SEQUENCE: 5

```
Gly Gly Gly Gly Ser Ser Ser
1               5
```

<210> SEQ ID NO 6
<211> LENGTH: 15
<212> TYPE: PRT
<213> ORGANISM: Artificial Sequence
<220> FEATURE:
<223> OTHER INFORMATION: Synthetic Linker

<400> SEQUENCE: 6

```
Gly Gly Gly Gly Ser Gly Gly Gly Ser Gly Gly Gly Gly Ser
1               5                   10                  15
```

<210> SEQ ID NO 7
<211> LENGTH: 20
<212> TYPE: PRT
<213> ORGANISM: Artificial Sequence

```
<220> FEATURE:
<223> OTHER INFORMATION: Synthetic Linker

<400> SEQUENCE: 7

Gly Gly Gly Gly Ser Gly Gly Gly Ser Gly Gly Gly Ser Gly
1               5                   10                  15

Gly Gly Gly Ser
            20

<210> SEQ ID NO 8
<211> LENGTH: 6
<212> TYPE: PRT
<213> ORGANISM: Artificial Sequence
<220> FEATURE:
<223> OTHER INFORMATION: Synthetic Linker

<400> SEQUENCE: 8

Leu Ile Lys Met Lys Pro
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic Linker

<400> SEQUENCE: 9

Gln Pro Gln Gly Leu Ala
1               5

<210> SEQ ID NO 10
<211> LENGTH: 657
<212> TYPE: PRT
<213> ORGANISM: Homo sapiens

<400> SEQUENCE: 10

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
                20                  25                  30

Thr Asp Tyr Thr Ala Glu Cys Lys Pro Gln Val Thr Arg Gly Asp Val
            35                  40                  45

Phe Thr Met Pro Glu Asp Glu Tyr Thr Val Tyr Asp Asp Gly Glu Glu
        50                  55                  60

Lys Asn Asn Ala Thr Val His Glu Gln Val Gly Gly Pro Ser Leu Thr
65                  70                  75                  80

Ser Asp Leu Gln Ala Gln Ser Lys Gly Asn Pro Glu Gln Thr Pro Val
                85                  90                  95

Leu Lys Pro Glu Glu Glu Ala Pro Ala Pro Glu Val Gly Ala Ser Lys
            100                 105                 110

Pro Glu Gly Ile Asp Ser Arg Pro Glu Thr Leu His Pro Gly Arg Pro
        115                 120                 125

Gln Pro Pro Ala Glu Glu Glu Leu Cys Ser Gly Lys Pro Phe Asp Ala
    130                 135                 140

Phe Thr Asp Leu Lys Asn Gly Ser Leu Phe Ala Phe Arg Gly Gln Tyr
145                 150                 155                 160

Cys Tyr Glu Leu Asp Glu Lys Ala Val Arg Pro Gly Tyr Pro Lys Leu
                165                 170                 175
```

-continued

```
Ile Arg Asp Val Trp Gly Ile Glu Gly Pro Ile Asp Ala Ala Phe Thr
            180                 185                 190
Arg Ile Asn Cys Gln Gly Lys Thr Tyr Leu Phe Lys Gly Ser Gln Tyr
        195                 200                 205
Trp Arg Phe Glu Asp Gly Val Leu Asp Pro Asp Tyr Pro Arg Asn Ile
    210                 215                 220
Ser Asp Gly Phe Asp Gly Ile Pro Asp Asn Val Asp Ala Ala Leu Ala
225                 230                 235                 240
Leu Pro Ala His Ser Tyr Ser Gly Arg Glu Arg Val Tyr Phe Phe Lys
                245                 250                 255
Gly Lys Gln Tyr Trp Glu Tyr Gln Phe Gln His Gln Pro Ser Gln Glu
            260                 265                 270
Glu Cys Glu Gly Ser Ser Leu Ser Ala Val Phe Glu His Phe Ala Met
        275                 280                 285
Met Gln Arg Asp Ser Trp Glu Asp Ile Phe Glu Leu Leu Phe Trp Gly
    290                 295                 300
Arg Thr Ser Ala Gly Thr Arg Gln Pro Gln Phe Ile Ser Arg Asp Trp
305                 310                 315                 320
His Gly Val Pro Gly Gln Val Asp Ala Ala Met Ala Gly Arg Ile Tyr
                325                 330                 335
Ile Ser Gly Met Ala Pro Arg Pro Ser Leu Ala Lys Lys Gln Arg Phe
            340                 345                 350
Arg His Arg Asn Arg Lys Gly Tyr Arg Ser Gln Arg Gly His Ser Arg
        355                 360                 365
Gly Arg Asn Gln Asn Ser Arg Arg Pro Ser Arg Ala Met Trp Leu Ser
    370                 375                 380
Leu Phe Ser Ser Glu Glu Ser Asn Leu Gly Ala Asn Asn Tyr Asp Asp
385                 390                 395                 400
Tyr Arg Met Asp Trp Leu Val Pro Ala Thr Cys Glu Pro Ile Gln Ser
                405                 410                 415
Val Phe Phe Phe Ser Gly Asp Lys Tyr Tyr Arg Val Asn Leu Arg Thr
            420                 425                 430
Arg Arg Val Asp Thr Val Asp Pro Pro Tyr Pro Arg Ser Ile Ala Gln
        435                 440                 445
Tyr Trp Leu Gly Cys Pro Ala Pro Gly His Leu Gly Gly Gly Gly Ser
    450                 455                 460
Gly Gly Gly Gly Ser Gly Gly Gly Ser Gly Gly Gly Gly Ser Cys
465                 470                 475                 480
Asn Asp Met Thr Pro Glu Gln Met Ala Thr Asn Val Asn Cys Ser Ser
                485                 490                 495
Pro Glu Arg His Thr Arg Ser Tyr Asp Tyr Met Glu Gly Gly Asp Ile
            500                 505                 510
Arg Val Arg Arg Leu Phe Cys Arg Thr Gln Trp Tyr Leu Arg Ile Asp
        515                 520                 525
Lys Arg Gly Lys Val Lys Gly Thr Gln Glu Met Lys Asn Asn Tyr Asn
    530                 535                 540
Ile Met Glu Ile Arg Thr Val Ala Val Gly Ile Val Ala Ile Lys Gly
545                 550                 555                 560
Val Glu Ser Glu Phe Tyr Leu Ala Met Asn Lys Glu Gly Lys Leu Tyr
                565                 570                 575
Ala Lys Lys Glu Cys Asn Glu Asp Cys Asn Phe Lys Glu Leu Ile Leu
            580                 585                 590
```

```
Glu Asn His Tyr Asn Thr Tyr Ala Ser Ala Lys Trp Thr His Asn Gly
            595                 600                 605

Gly Glu Met Phe Val Ala Leu Asn Gln Lys Gly Ile Pro Val Arg Gly
610                 615                 620

Lys Lys Thr Lys Lys Glu Gln Lys Thr Ala His Phe Leu Pro Met Ala
625                 630                 635                 640

Ile Thr Gly Gly Gly Ser Gly Gly Gly His His His His His
                645                 650                 655

His

<210> SEQ ID NO 11
<211> LENGTH: 509
<212> TYPE: PRT
<213> ORGANISM: Homo sapiens

<400> SEQUENCE: 11

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
                20                  25                  30

Thr Asp Tyr Thr Ala Glu Cys Lys Pro Gln Val Thr Arg Gly Asp Val
            35                  40                  45

Phe Thr Met Pro Glu Asp Glu Tyr Thr Val Tyr Asp Asp Gly Glu Glu
    50                  55                  60

Lys Asn Asn Ala Thr Val His Glu Gln Val Gly Gly Pro Ser Leu Thr
65                  70                  75                  80

Ser Asp Leu Gln Ala Gln Ser Lys Gly Asn Pro Glu Gln Thr Pro Val
                85                  90                  95

Leu Lys Pro Glu Glu Glu Ala Pro Ala Pro Glu Val Gly Ala Ser Lys
            100                 105                 110

Pro Glu Gly Ile Asp Ser Arg Pro Glu Thr Leu His Pro Gly Arg Pro
    115                 120                 125

Gln Pro Pro Ala Glu Glu Glu Leu Cys Ser Gly Lys Pro Phe Asp Ala
130                 135                 140

Phe Thr Asp Leu Lys Asn Gly Ser Leu Phe Ala Phe Arg Gly Gln Tyr
145                 150                 155                 160

Cys Tyr Glu Leu Asp Glu Lys Ala Val Arg Pro Gly Tyr Pro Lys Leu
                165                 170                 175

Ile Arg Asp Val Trp Gly Ile Glu Gly Pro Ile Asp Ala Ala Phe Thr
            180                 185                 190

Arg Ile Asn Cys Gln Gly Lys Thr Tyr Leu Phe Lys Gly Ser Gln Tyr
    195                 200                 205

Trp Arg Phe Glu Asp Gly Val Leu Asp Pro Asp Tyr Pro Arg Asn Ile
210                 215                 220

Ser Asp Gly Phe Asp Gly Ile Pro Asp Asn Val Asp Ala Ala Leu Ala
225                 230                 235                 240

Leu Pro Ala His Ser Tyr Ser Gly Arg Glu Arg Val Tyr Phe Phe Lys
                245                 250                 255

Gly Lys Gln Tyr Trp Glu Tyr Gln Phe Gln His Gln Pro Ser Gln Glu
            260                 265                 270

Glu Cys Glu Gly Ser Ser Leu Ser Ala Val Phe Glu His Phe Ala Met
    275                 280                 285

Met Gln Arg Asp Ser Trp Glu Asp Ile Phe Glu Leu Leu Phe Trp Gly
290                 295                 300
```

-continued

```
Arg Thr Ser Ala Gly Thr Arg Gly Gly Gly Ser Gly Gly Gly
305                 310                 315                 320

Ser Gly Gly Gly Ser Gly Gly Gly Ser Cys Asn Asp Met Thr
            325                 330                 335

Pro Glu Gln Met Ala Thr Asn Val Asn Cys Ser Ser Pro Glu Arg His
            340                 345                 350

Thr Arg Ser Tyr Asp Tyr Met Glu Gly Gly Asp Ile Arg Val Arg Arg
            355                 360                 365

Leu Phe Cys Arg Thr Gln Trp Tyr Leu Arg Ile Asp Lys Arg Gly Lys
            370                 375                 380

Val Lys Gly Thr Gln Glu Met Lys Asn Asn Tyr Asn Ile Met Glu Ile
385                 390                 395                 400

Arg Thr Val Ala Val Gly Ile Val Ala Ile Lys Gly Val Glu Ser Glu
            405                 410                 415

Phe Tyr Leu Ala Met Asn Lys Glu Gly Lys Leu Tyr Ala Lys Lys Glu
            420                 425                 430

Cys Asn Glu Asp Cys Asn Phe Lys Glu Leu Ile Leu Glu Asn His Tyr
            435                 440                 445

Asn Thr Tyr Ala Ser Ala Lys Trp Thr His Asn Gly Gly Glu Met Phe
450                 455                 460

Val Ala Leu Asn Gln Lys Gly Ile Pro Val Arg Gly Lys Lys Thr Lys
465                 470                 475                 480

Lys Glu Gln Lys Thr Ala His Phe Leu Pro Met Ala Ile Thr Gly Gly
            485                 490                 495

Gly Gly Ser Gly Gly Gly His His His His His His
            500                 505
```

<210> SEQ ID NO 12
<211> LENGTH: 324
<212> TYPE: PRT
<213> ORGANISM: Homo sapiens

<400> SEQUENCE: 12

```
Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
            35                  40                  45

Phe Thr Met Pro Glu Asp Glu Tyr Thr Val Tyr Asp Asp Gly Glu Glu
50                  55                  60

Lys Asn Asn Ala Thr Val His Glu Gln Val Gly Gly Pro Ser Leu Thr
65                  70                  75                  80

Ser Asp Leu Gln Ala Gln Ser Lys Gly Asn Pro Glu Gln Thr Pro Val
            85                  90                  95

Leu Lys Pro Glu Glu Glu Ala Pro Ala Pro Glu Val Gly Ala Ser Lys
            100                 105                 110

Pro Glu Gly Ile Asp Ser Arg Pro Glu Thr Leu His Pro Gly Gly Gly
            115                 120                 125

Gly Gly Ser Gly Gly Gly Ser Gly Gly Gly Ser Gly Gly Gly
            130                 135                 140

Gly Ser Cys Asn Asp Met Thr Pro Glu Gln Met Ala Thr Asn Val Asn
145                 150                 155                 160

Cys Ser Ser Pro Glu Arg His Thr Arg Ser Tyr Asp Tyr Met Glu Gly
            165                 170                 175
```

Gly Asp Ile Arg Val Arg Arg Leu Phe Cys Arg Thr Gln Trp Tyr Leu
            180                 185                 190

Arg Ile Asp Lys Arg Gly Lys Val Lys Gly Thr Gln Glu Met Lys Asn
        195                 200                 205

Asn Tyr Asn Ile Met Glu Ile Arg Thr Val Ala Val Gly Ile Val Ala
    210                 215                 220

Ile Lys Gly Val Glu Ser Glu Phe Tyr Leu Ala Met Asn Lys Glu Gly
225                 230                 235                 240

Lys Leu Tyr Ala Lys Lys Glu Cys Asn Glu Asp Cys Asn Phe Lys Glu
                245                 250                 255

Leu Ile Leu Glu Asn His Tyr Asn Thr Tyr Ala Ser Ala Lys Trp Thr
            260                 265                 270

His Asn Gly Gly Glu Met Phe Val Ala Leu Asn Gln Lys Gly Ile Pro
        275                 280                 285

Val Arg Gly Lys Lys Thr Lys Lys Glu Gln Lys Thr Ala His Phe Leu
    290                 295                 300

Pro Met Ala Ile Thr Gly Gly Gly Ser Gly Gly Gly His His
305                 310                 315                 320

His His His His

<210> SEQ ID NO 13
<211> LENGTH: 262
<212> TYPE: PRT
<213> ORGANISM: Homo sapiens

<400> SEQUENCE: 13

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Glu Asp Glu Tyr Thr Val Tyr Asp Asp Gly Glu Glu
    50                  55                  60

Gly Gly Gly Gly Ser Gly Gly Gly Ser Gly Gly Gly Ser Gly
65                  70                  75                  80

Gly Gly Ser Cys Asn Asp Met Thr Pro Glu Gln Met Ala Thr Asn
                85                  90                  95

Val Asn Cys Ser Ser Pro Glu Arg His Thr Arg Ser Tyr Asp Tyr Met
            100                 105                 110

Glu Gly Gly Asp Ile Arg Val Arg Arg Leu Phe Cys Arg Thr Gln Trp
        115                 120                 125

Tyr Leu Arg Ile Asp Lys Arg Gly Lys Val Lys Gly Thr Gln Glu Met
    130                 135                 140

Lys Asn Asn Tyr Asn Ile Met Glu Ile Arg Thr Val Ala Val Gly Ile
145                 150                 155                 160

Val Ala Ile Lys Gly Val Glu Ser Glu Phe Tyr Leu Ala Met Asn Lys
                165                 170                 175

Glu Gly Lys Leu Tyr Ala Lys Lys Glu Cys Asn Glu Asp Cys Asn Phe
            180                 185                 190

Lys Glu Leu Ile Leu Glu Asn His Tyr Asn Thr Tyr Ala Ser Ala Lys
        195                 200                 205

Trp Thr His Asn Gly Gly Glu Met Phe Val Ala Leu Asn Gln Lys Gly
    210                 215                 220

```
Ile Pro Val Arg Gly Lys Lys Thr Lys Lys Glu Gln Lys Thr Ala His
225                 230                 235                 240

Phe Leu Pro Met Ala Ile Thr Gly Gly Gly Ser Gly Gly Gly Gly
            245                 250                 255

His His His His His His
            260

<210> SEQ ID NO 14
<211> LENGTH: 316
<212> TYPE: PRT
<213> ORGANISM: Homo sapiens

<400> SEQUENCE: 14

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
                20                  25                  30

Thr Asp Tyr Thr Ala Glu Cys Lys Pro Gln Val Thr Arg Gly Asp Val
            35                  40                  45

Phe Thr Met Pro Glu Asp Glu Tyr Thr Val Tyr Asp Asp Gly Glu Glu
        50                  55                  60

Gly Gly Gly Gly Ser Gly Gly Gly Ser Gly Gly Gly Ser Gly
65                  70                  75                  80

Gly Gly Gly Ser Arg Pro Ser Leu Ala Lys Lys Gln Arg Phe Arg His
                85                  90                  95

Arg Asn Arg Lys Gly Tyr Arg Ser Gln Arg Gly His Ser Arg Gly Arg
                100                 105                 110

Asn Gln Asn Ser Arg Arg Gly Gly Gly Ser Gly Gly Gly Gly Ser
            115                 120                 125

Gly Gly Gly Gly Ser Gly Gly Gly Ser Cys Asn Asp Met Thr Pro
        130                 135                 140

Glu Gln Met Ala Thr Asn Val Asn Cys Ser Ser Pro Glu Arg His Thr
145                 150                 155                 160

Arg Ser Tyr Asp Tyr Met Glu Gly Gly Asp Ile Arg Val Arg Arg Leu
                165                 170                 175

Phe Cys Arg Thr Gln Trp Tyr Leu Arg Ile Asp Lys Arg Gly Lys Val
            180                 185                 190

Lys Gly Thr Gln Glu Met Lys Asn Asn Tyr Asn Ile Met Glu Ile Arg
        195                 200                 205

Thr Val Ala Val Gly Ile Val Ala Ile Lys Gly Val Glu Ser Glu Phe
210                 215                 220

Tyr Leu Ala Met Asn Lys Glu Gly Lys Leu Tyr Ala Lys Lys Glu Cys
225                 230                 235                 240

Asn Glu Asp Cys Asn Phe Lys Glu Leu Ile Leu Glu Asn His Tyr Asn
                245                 250                 255

Thr Tyr Ala Ser Ala Lys Trp Thr His Asn Gly Gly Glu Met Phe Val
            260                 265                 270

Ala Leu Asn Gln Lys Gly Ile Pro Val Arg Gly Lys Lys Thr Lys Lys
        275                 280                 285

Glu Gln Lys Thr Ala His Phe Leu Pro Met Ala Ile Thr Gly Gly Gly
    290                 295                 300

Gly Ser Gly Gly Gly Gly His His His His His
305                 310                 315
```